US010695319B2

(12) United States Patent
Liu et al.

(10) Patent No.: US 10,695,319 B2
(45) Date of Patent: Jun. 30, 2020

(54) GLUCOSE CONJUGATES OF TRIPTOLIDE, ANALOGS AND USES THEREOF

(71) Applicants: The Johns Hopkins University, Baltimore, MD (US); Shanghai Institute of Organic Chemistry, Chinese Academy of Sciences, Shanghai (CN)

(72) Inventors: Jun Liu, Baltimore, MD (US); Qingli He, Baltimore, MD (US); Martin G. Pomper, Baltimore, MD (US); Il Minn, Baltimore, MD (US); Biao Yu, Baltimore, MD (US); Qiaoling Wang, Baltimore, MD (US)

(73) Assignees: The Johns Hopkins University, Baltimore, MD (US); Shanghai Institute of Organic Chemistry, Chinese Academy of Sciences, Shanghai (CN)

(*) Notice: Subject to any disclaimer, the term of this patent is extended or adjusted under 35 U.S.C. 154(b) by 0 days.

(21) Appl. No.: 16/074,750

(22) PCT Filed: Feb. 3, 2017

(86) PCT No.: PCT/US2017/016527
§ 371 (c)(1),
(2) Date: Aug. 1, 2018

(87) PCT Pub. No.: WO2017/136739
PCT Pub. Date: Aug. 10, 2017

(65) Prior Publication Data
US 2019/0038596 A1 Feb. 7, 2019

Related U.S. Application Data

(60) Provisional application No. 62/291,416, filed on Feb. 4, 2016.

(51) Int. Cl.
| | |
|---|---|
| *A01N 43/04* | (2006.01) |
| *A61K 31/70* | (2006.01) |
| *A61K 31/365* | (2006.01) |
| *C07D 493/22* | (2006.01) |
| *C07J 73/00* | (2006.01) |
| *A61K 47/54* | (2017.01) |
| *A61P 35/00* | (2006.01) |
| *C07H 15/26* | (2006.01) |

(52) U.S. Cl.
CPC .......... *A61K 31/365* (2013.01); *A61K 47/549* (2017.08); *A61P 35/00* (2018.01); *C07D 493/22* (2013.01); *C07H 15/26* (2013.01); *C07J 73/003* (2013.01)

(58) Field of Classification Search
None
See application file for complete search history.

(56) References Cited

U.S. PATENT DOCUMENTS

| 6,218,367 B1 * | 4/2001 | Jacob | ............ C07H 15/26 514/25 |
|---|---|---|---|
| 6,569,893 B2 | 5/2003 | Dai et al. | |
| 6,620,843 B2 | 9/2003 | Fidler | |
| 9,150,600 B2 | 10/2015 | Georg et al. | |
| 2002/0099051 A1 | 7/2002 | Fidler | |
| 2014/0107077 A1 | 4/2014 | Georg et al. | |

OTHER PUBLICATIONS

Zhou et al. Journal of Drug Targeting (2014), vol. 22, pp. 200-210.*
Pubchem Open Chemistry Database, Compound Summary for CID 101239577, "(14-S)-14-O-beta-D-Glucopyranosyltriptolide" (Create Date: Dec. 18, 2015, Modify Date Mar. 18, 2017), 10 pages, National Institutes of Health, U.S. National Library of Medicine.
European Partial Supplementary Search Report dated Aug. 19, 2019, regarding EP 17 748 283.3.
Hamada, Hiroki et al: "Chemo-enzymatic Synthesis of Propionyl-ester-linked Taxol-monosaccharide Conjugate and its Drug Delivery System Using Hybrid-Bio-nanocapsules Targeting Brain Glioma Cells": Clinical Medicine Insights: Women's Health, 2013, vol. 6, pp. 71-75. doi:10.4137/CMWH.S8213.
Liu, Pengxing et al.: "Highly water-soluble platinum(II) complexes as GLUT substrates for targeted therapy: improved anticancer efficacy and transporter-mediated cytotoxic properties"; Chem. Commun., Mar. 25, 2013, vol. 49, No. 24, pp. 2421-2423, XP-002793228.
Liu, Der-Zen et al.: "Synthess of 2'-paclitaxel methyl 2-glucopyranosyl succinate for specific targeted delivery to cancer cells"; Bioorganic & Medicinal Chemistry Letters, January 19, 2007, vol. 17, No. 3, pp. 617-620. XP005835904.

* cited by examiner

*Primary Examiner* — Patrick T Lewis
(74) *Attorney, Agent, or Firm* — DLA Piper LLP (US)

(57) ABSTRACT

Provided are compounds generated by conjugation of triptolide with glucose to form glucose-triptolide conjugates, provides compounds with effective anti-proliferative activity and improved tolerability as compared to naturally occurring triptolide compounds.

33 Claims, 4 Drawing Sheets

GLUCOSE CONJUGATES OF TRIPTOLIDE, ANALOGS AND USES THEREOF

CROSS-REFERENCE TO RELATED APPLICATIONS

This application is a 35 USC § 371 National Stage application of International Application No. PCT/US2017/016527 filed Feb. 3, 2017, now pending; which claims the benefit under 35 USC § 119(e) to U.S. Application Ser. No. 62/291,416 filed Feb. 4, 2016. The disclosure of each of the prior applications is considered part of and is incorporated by reference in the disclosure of this application.

BACKGROUND OF THE INVENTION

Field of the Invention

The invention relates generally to anti-cancer compounds and more specifically to glucose conjugates of triptolide and analogs thereof, and methods of treating cancer using such compounds.

Background Information

Triptolide is an active component from the traditional Chinese medicinal plant Thunder God Vine. It has been shown to possess anti-inflammatory, immunosuppressive and anticancer activities, among others. Its molecular target has been identified as the XPB (ERCC3) subunit of the general transcription factor TFIIH. It works by blocking RNAPII transcription initiation and nucleoside excision repair. Triptolide and analogs have been developed as new anticancer and immunosuppressive drugs. Unfortunately, dose-limiting toxicity and insolubility have been major hurdles for its development as a new drug.

SUMMARY OF THE INVENTION

The present invention is based on the seminal discovery that conjugation of triptolide with glucose to form glucose-triptolide conjugates provides compounds with effective anti-proliferative activity and improved tolerability as compared to naturally occurring triptolide compounds.

In one embodiment, the invention provides a method of treating cancer in a subject comprising administering to the subject an anti-proliferative effective amount of a glucose-triptolide conjugate compound, thereby treating the cancer.

The glucose-triptolide conjugate compounds have the structure of Formula I:

T&A-L$_1$-Sugar    (I)

wherein the T&A moiety is triptolide or one of its analogs, and can be selected from compounds 1 to 18:

1

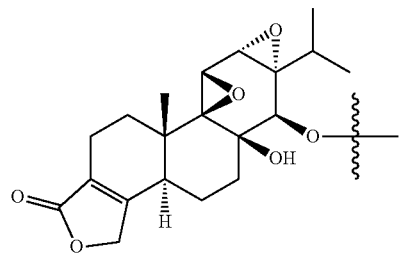

2

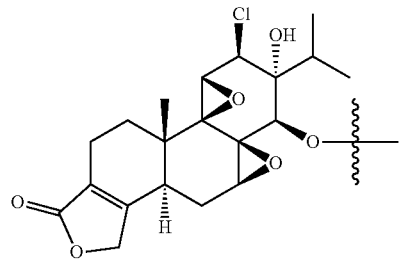

3

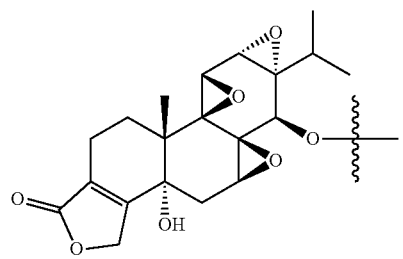

4

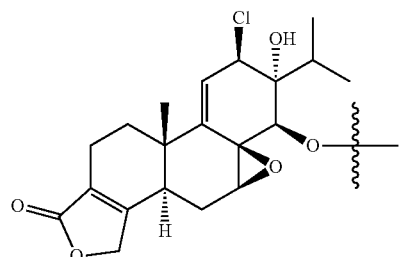

5

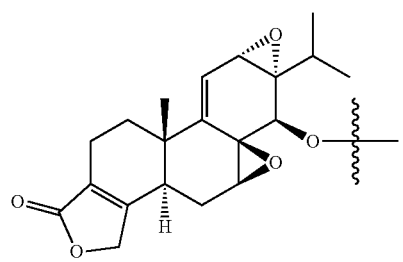

6

7

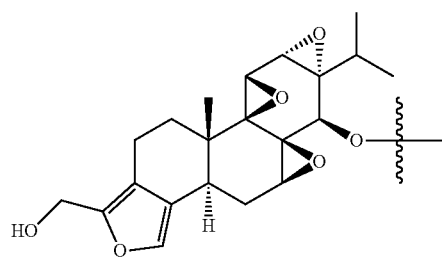

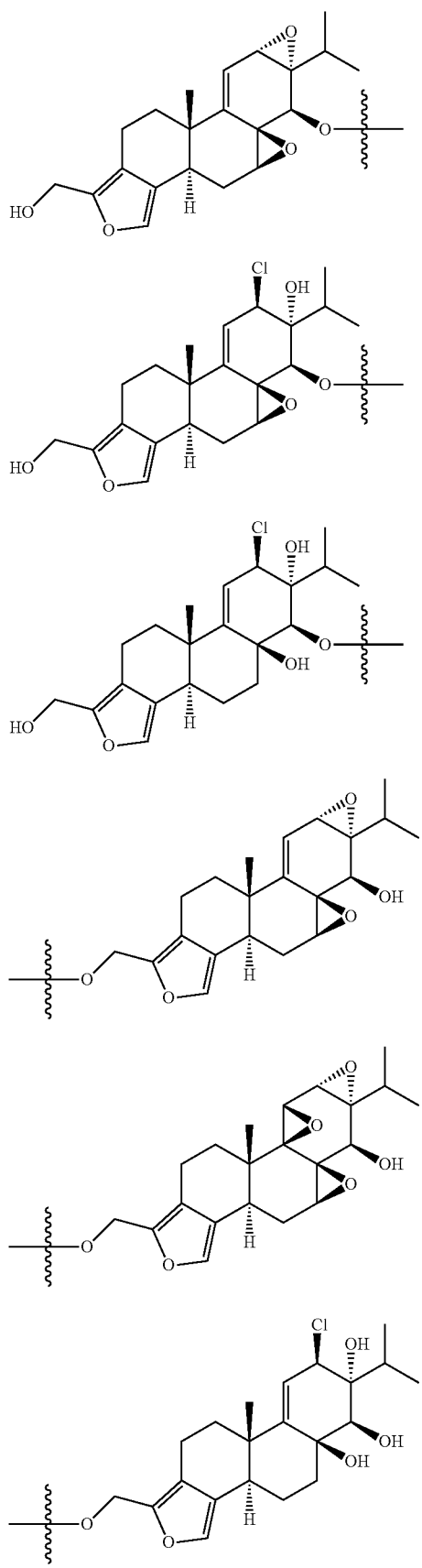
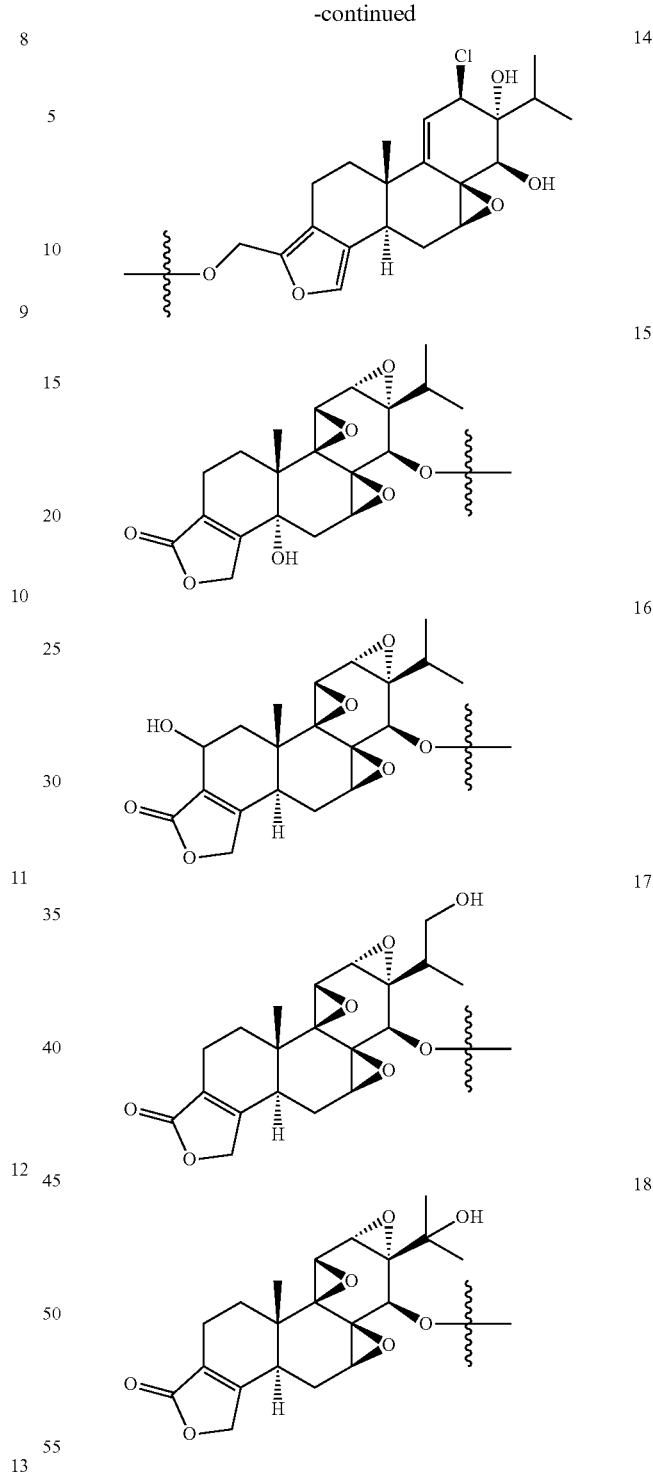

wherein $L_1$ can be selected from —X—Y—Z—, wherein X and Z can individually and independently be a direct bond, —$CH_2$—, —C(O)—, —SO—, —$SO_2$—, —OPO—, —$OPO_2$—, and wherein Y is a direct bond, a substituted or unsubstituted —($C_1$-$C_6$)alkyl-, substituted or unsubstituted —$(CH_2)_n$O($C_1$-$C_6$)alkyl-, substituted or unsubstituted —$(CH_2)_n$C(O)($C_1$-$C_6$)alkyl-, substituted or unsubstituted —$(CH_2)_n$C(O)O($C_1$-$C_6$)alkyl-, substituted or unsubstituted —$(CH_2)_n$NH($C_1$-$C_6$)alkyl-, substituted or unsubstituted —$(CH_2)_n$C(O)NH($C_1$-$C_6$)alkyl-, substituted or unsubstituted —$(CH_2)_n$S($C_1$-$C_6$)alkyl-, substituted or unsubstituted —(CH$_2$)$_n$C(O)(CH$_2$)$_n$S(C$_1$-C$_6$)alkyl-, substituted or unsubstituted —(C$_2$-C$_6$)alkenyl-, substituted or unsubstituted —(CH$_2$)$_n$O(C$_2$-C$_6$)alkenyl-, substituted or unsubstituted —(CH$_2$)$_n$C(O)(C$_2$-C$_6$)alkenyl-, substituted or unsubstituted —(CH$_2$)$_n$C(O)O(C$_2$-C$_6$)alkenyl-, substituted or unsubstituted —(CH$_2$)$_n$NH(C$_2$-C$_6$)alkenyl-, substituted or unsubstituted —(CH$_2$)$_n$C(O)NH(C$_2$-C$_6$)alkenyl-, substituted or unsubstituted —(CH$_2$)$_n$S(C$_2$-C$_6$)alkenyl-, substituted or unsubstituted —(CH$_2$)$_n$C(O)(CH$_2$)$_n$S(C$_2$-C$_6$)alkenyl-, substituted or unsubstituted —(C$_2$-C$_6$)alkynyl-, substituted or unsubstituted —(CH$_2$)$_n$O(C$_2$-C$_6$)alkynyl-, substituted or unsubstituted —(CH$_2$)$_n$C(O)(C$_2$-C$_6$)alkynyl-, substituted or unsubstituted —(CH$_2$)$_n$C(O)O(C$_2$-C$_6$)alkynyl-, substituted or unsubstituted —(CH$_2$)$_n$NH(C$_2$-C$_6$)alkynyl-, substituted or unsubstituted —(CH$_2$)$_n$C(O)NH(C$_2$-C$_6$)alkynyl-, substituted or unsubstituted —(CH$_2$)$_n$S(C$_2$-C$_6$)alkynyl-, substituted or unsubstituted —(CH$_2$)$_n$C(O)(CH$_2$)$_n$S(C$_2$-C$_6$)alkynyl-, wherein each alkyl, alkenyl and alkynyl group may be optionally substituted with alkyl, alkoxy, amino, hydroxyl, oxo, aryl, heteroaryl, carboxyl, cyano, nitro, or trifluoromethyl;

wherein the sugar can be selected from compounds 19 to 53:

19
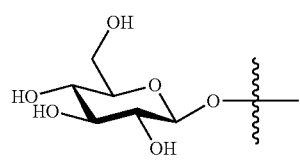

20
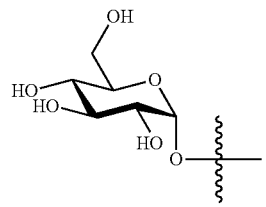

21
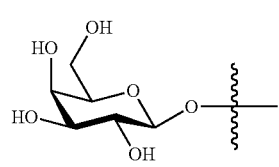

22
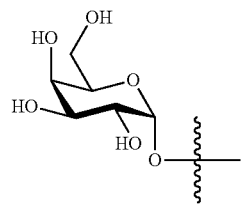

23
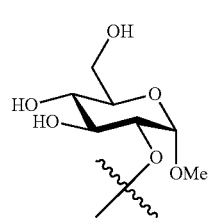

-continued

24
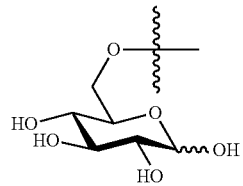

25
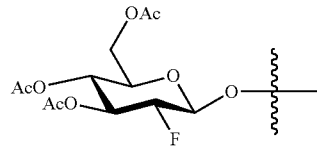

26
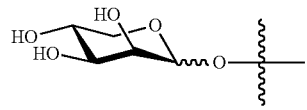

27
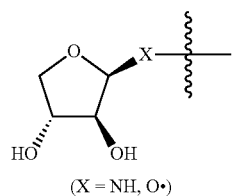
(X = NH, O•)

28
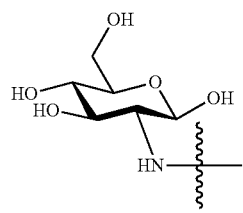

29
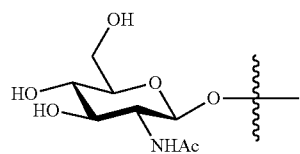

30
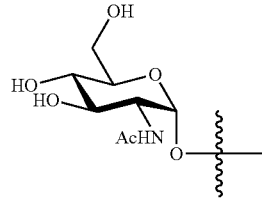

31
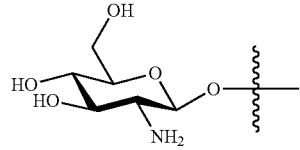

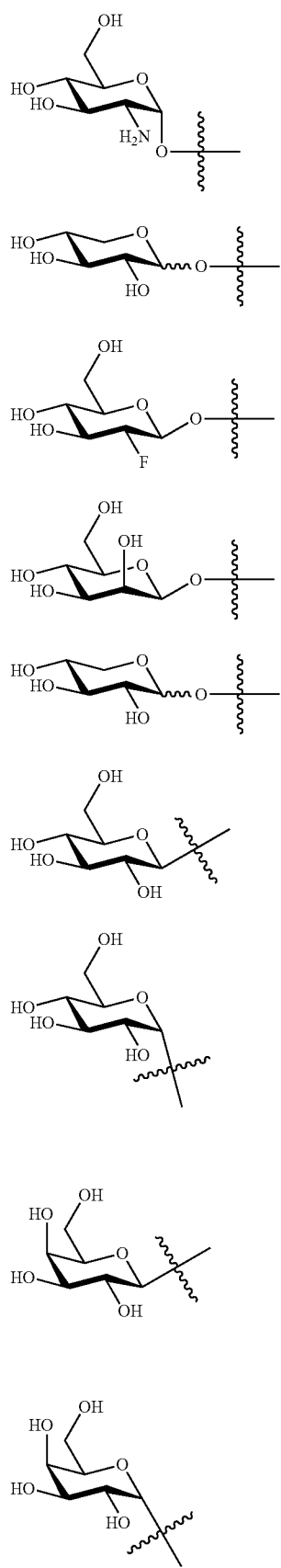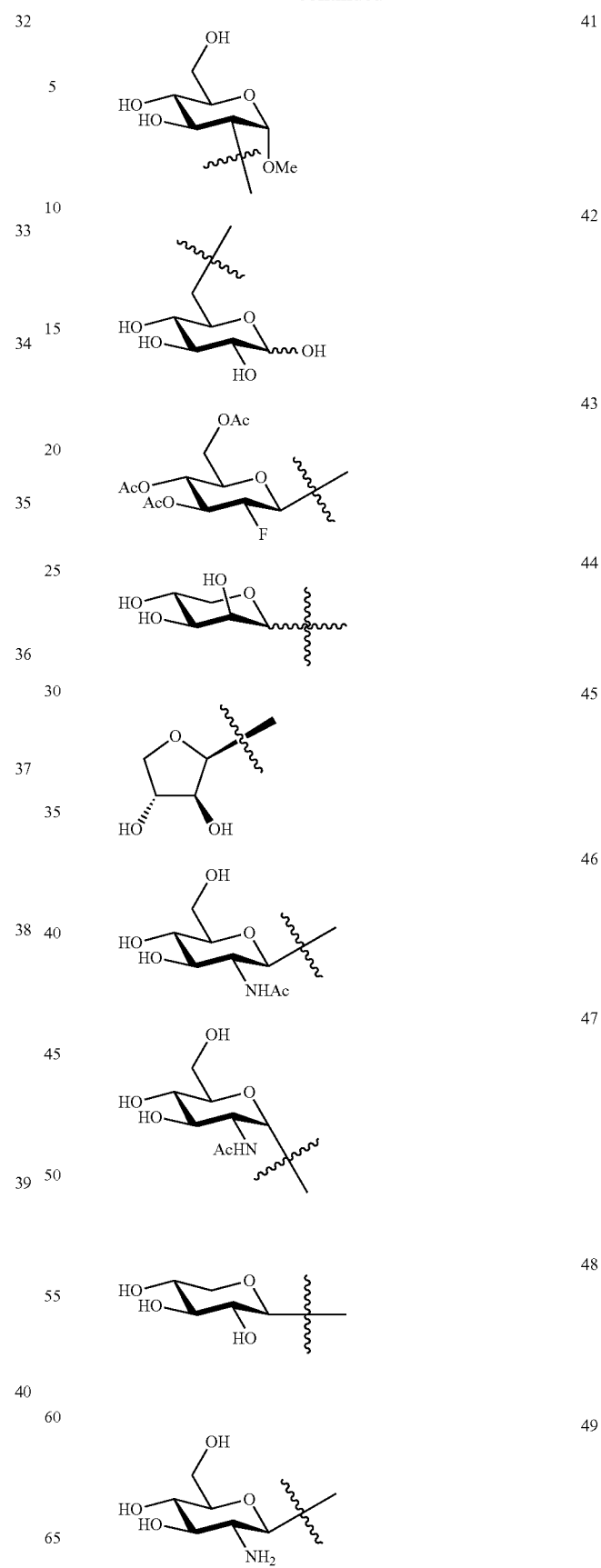

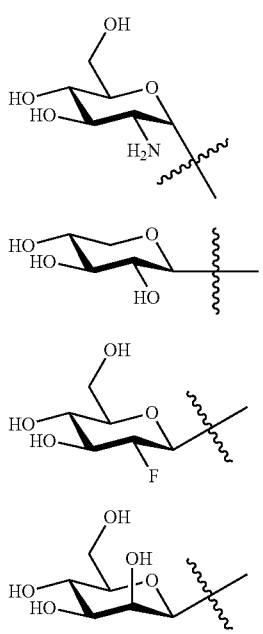

The cancer may be one of the following, but not limited to bladder cancer, breast cancer, ovarian cancer, pancreatic cancer, and gastric cancer, cervical cancer, colon cancer, endometrial cancer, head and neck cancer, lung cancer, melanoma, multiple myeloma, leukemia, non-hodgkin's lymphoma, prostate cancer, rectal cancer, malignant melanomas, alimentary/gastrointestinal tract cancer, liver cancer, skin cancer, lymphoma, kidney cancer, muscle cancer, bone cancer, brain cancer, eye or ocular cancer, rectal cancer, colon cancer, cervical cancer, bladder cancer, oral cancer, benign and malignant tumors, stomach cancer, corpus uteri, testicular cancer, renal cancer, throat cancer, acute lymphocytic leukemia, acute myelogenous leukemia, Ewing's Sarcoma, Kaposi's Sarcoma, basal cell carcinoma and squamous cell carcinoma, small cell lung cancer, choriocarcinoma, rhabdomyosarcoma, angiosarcoma, hemangioendothelioma, Wilms Tumor, neuroblastoma, mouth/pharynx cancer, esophageal cancer, larynx cancer, neurofibromatosis, tuberous sclerosis, hemangiomas, and lymphangiogenesis.

In another embodiment, the cancer is prostate cancer.
In another embodiment, the cancer is metastatic cancer.
In another embodiment, T&A moiety is compound 1 and the sugar is compound 19, 20, 37 or 38.
In another embodiment, $L_1$ is a direct bond, —COCH$_2$CH$_2$CO—, or —CH$_2$—.
In another embodiment, T&A moiety is compound 1 and the sugar is compound 19.
In another embodiment, the glucose triptolide conjugate compound has a Formula G1-9. In a preferred embodiment the compound is Formula G4. Formula G1-9 are illustrated in the structures provided herein. The invention also provides a pharmaceutical composition comprising the compounds listed above.

The method of treatment includes administration intravenously, such as at a dosage of about 0.1 mg/kg to 2 mg/kg per dosage. In one aspect, the compound is administered once daily for up to about 4 weeks. The method may further include administering a chemotherapeutic compound, for example, prior to, simultaneously with, or following administration of a compound of the invention.

In another embodiment, the method of synthesizing a glucose-triptolide conjugate compound includes synthetic scheme I, II or III. These schemes are provided herein.

In another embodiment, an anti-proliferative effective amount of a glucose-triptolide conjugate compound is administered to a subject in a method to treat possible organ rejection in subjects that have undergone an organ transplant.

In another embodiment, an anti-proliferative effective amount of a glucose-triptolide conjugate compound is administered to a subject in a method to treat autoimmune diseases.

Examples of immune related diseases that can be treated include but are not limited to: Acute disseminated encephalomyelitis (ADEM), Addison's disease, Ankylosing spondylitis, Antiphospholipid antibody syndrome, Autoimmune hemolytic anemia, Autoimmune hepatitis, Autoimmune inner ear disease, Autoimmune Lymphoproliferative Syndrome (ALPS), Autoimmune polyendocrine/polyglandular syndrome, Autoimmune thrombocytoipenia purpura, Balo disease, Behçet disease, Bullous pemphigoid, Cardiomyopathy, Celiac sprue-dermatitis herpetiformis, Chronic fatigue immune dysfunction syndrome (CFIDS), Chronic inflammatory demyelinating neuropathy, Cicatrical pemphigoid, Coeliac disease, Cold agglutinin disease, CREST syndrome, Crohn's disease, Cystic fibrosis, Degos disease, Dermatomyositis, Diabetes (Type I or Juvenile onset), Early onset dementia, Eczema, Endotoxin shock, Essential mixed cryoglobulinemia, Familial Mediterranean fever, Fibromyalgia, Fibromyositis, Goodpasture's syndrome, Graves' disease, Guillain-Barrê syndrome (GBS), Hashimoto's thyroidosis, Hidradenitis suppurativa, Idiopathic pulmonary fibrosis, Idiopathic thrombocytopenic purpura, IgA nephropathy, Lambert-Eaton Myasthenic Syndrome, Leukemia, Lichen planus, Ménière disease, Mixed connective tissue disease, Multiple sclerosis, Multiphasic disseminated encephalomyelitis, Myasthenia gravis, Neuromyelitis Optica, Paraneoplastic Syndromes, Pemphigus, Pemphigus vulgaris, Pernicious anemia, Polyarteritis nodosum, Polychondritis, Polymyalgia rhematica, Polymyositis, Primary agammaglobulinemia, Primary biliary cirrhosis, Plaque Psoriasis, Psoriatic arthritis, Raynaud phenomenon, Reiter syndrome, Restenosis following angioplasty, Rheumatic fever, Rheumatoid arthritis, Rheumatoid psoriasis, Sarcoidosis, Scleroderma, Sepsis, Sezary's disease, Sjögren's syndrome, Stiff-person syndrome, Lupus including Systemic lupus erythematosis (SLE), Takayasu arteritis, Temporal arteritis (also known as "giant cell arteritis"), Transplant or Allograft rejection, Ulcerative colitis, Uveitis, Vasculitis, Vitiligo, Graft vs Host disease, pustular psoriasis, and Wegener's granulomatosis (now termed Granulomatosis with Polyangiitis (GPA), inflammatory bowel disease, Acute necrotizing hemorrhagic leukoencephalitis, Agammaglobulinemia, Alopecia areata, Amyloidosis, Anti-GBM/Anti-TBM nephritis, Antiphospholipid syndrome (APS), Autoimmune angioedema, Autoimmune aplastic anemia, Autoimmune dysautonomia, Autoimmune hyperlipidemia, Autoimmune immunodeficiency, Autoimmune inner ear disease (AIED), Autoimmune myocarditis, Autoimmune oophoritis, Autoimmune pancreatitis, Autoimmune retinopathy, Autoimmune thyroid disease, Autoimmune urticarial, Axonal & neuronal neuropathies, Castleman disease, Celiac disease, Chagas disease, Chronic fatigue syndrome, Chronic inflammatory demyelinating polyneuropathy (CIDP), Chronic recurrent multifocal ostomyelitis (CRMO), Churg-Strauss syndrome, Cicatricial pemphigoid/benign mucosal pemphigoid, Cogans syndrome, Congenital heart block, Coxsackie myocarditis, CREST disease, Demyelinating neuropathies, Dermatitis herpetiformis, Devic's disease (neuromyelitis optica), Discoid lupus, Dressler's syndrome, Endometriosis, Eosinophilic esophagitis, Eosinophilic fasciitis, Erythema nodosum, Experimental allergic encephalomyelitis, Evans syndrome, Fibrosing alveolitis, Giant cell arteritis (temporal arteritis), Giant cell myocarditis, Glomerulonephritis, Granulomatosis with Polyangiitis (GPA) (formerly called Wegener's Granulomatosis), Hashimoto's encephalitis, Hashimoto's thyroiditis, Hemolytic anemia, Henoch-Schonlein purpura, Herpes gestationis, Hypogammaglobulinemia, Idiopathic thrombocytopenic purpura (ITP), IgG4-related sclerosing disease, Immunoregulatory lipoproteins, Inclusion body myositis, Interstitial cystitis, Juvenile arthritis, Juvenile diabetes (Type 1 diabetes), Juvenile myositis, Kawasaki syndrome, Lambert-Eaton syndrome, Leukocytoclastic vasculitis, Lichen sclerosus, Ligneous conjunctivitis, Linear IgA disease (LAD), Lupus (SLE), Lyme disease, chronic, Microscopic polyangiitis, Mooren's ulcer, Mucha-Habermann disease, Myositis, Narcolepsy, Neutropenia, Ocular cicatricial pemphigoid, Optic neuritis, Palindromic rheumatism, PANDAS (Pediatric Autoimmune Neuropsychiatric Disorders Associated with *Streptococcus*), Paraneoplastic cerebellar degeneration, Paroxysmal nocturnal hemoglobinuria (PNH), Parry Romberg syndrome, Parsonnage-Turner syndrome, Pars planitis (peripheral uveitis), Pemphigus, Peripheral neuropathy, Perivenous encephalomyelitis, POEMS syndrome, Type I, II, & III autoimmune polyglandular syndromes, Postmyocardial infarction syndrome, Postpericardiotomy syndrome, Progesterone dermatitis, Primary biliary cirrhosis, Primary sclerosing cholangitis, Psoriasis, Psoriatic arthritis, Idiopathic pulmonary fibrosis, Pyoderma gangrenosum, Pure red cell aplasia, Reactive Arthritis, Reflex sympathetic dystrophy, Relapsing polychondritis, Restless legs syndrome, Retroperitoneal fibrosis, Rheumatic fever, Schmidt syndrome, Scleritis, Sperm & testicular autoimmunity, Subacute bacterial endocarditis (SBE), Susac's syndrome, Sympathetic ophthalmia, Thrombocytopenic purpura (TTP), Tolosa-Hunt syndrome, Transverse myelitis, Type 1 diabetes, Undifferentiated connective tissue disease (UCTD) and Vesiculobullous dermatosis.

In another embodiment, a library of glucose conjugates of triptolide and analogs thereof, is used to screen for compounds for treating cancer.

In another embodiment, a library of glucose conjugates of triptolide and analogs thereof, is used to screen for compounds for treating possible organ rejection.

In another embodiment, a library of glucose conjugates of triptolide and analogs thereof, is used to screen for compounds for treating autoimmune disease.

DETAILED DESCRIPTION OF THE INVENTION

The present invention is based on trying to solve the issues of solubility and toxicity associated with triptolide. It was hypothesized that if triptolide could be conjugated to glucose, the two aforementioned problems associated with triptolide could be addressed. The glucose-triptolide conjugates would be preferentially taken up by cancer cells and they should also exhibit much higher water solubility due to the water solubility of glucose moiety.

As used herein, the term "cancer" or "cancerous growth" means the uncontrolled, abnormal growth of cells and includes within its scope all the well-known diseases that are caused by the uncontrolled and abnormal growth of cells. Non-limiting examples of common cancers include bladder cancer, breast cancer, ovarian cancer, pancreatic cancer, and gastric cancer, cervical cancer, colon cancer, endometrial cancer, head and neck cancer, lung cancer, melanoma, multiple myeloma, leukemia (e.g. myeloid, lymphocytic, myelocytic and lymphoblastic leukemias), non-hodgkin's lymphoma, prostate cancer, rectal cancer, and malignant melanomas.

In addition to invention compounds, one of skill in the art would recognize that chemotherapeutic agents can be used prior to, simultaneously with or following treatment with invention compounds. Illustrative agents include but are not limited to, taxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologs thereof. Therapeutic antibodies or other proteins are also envisioned in combination therapies of the invention.

The following examples are intended to illustrate but not limit the invention.

Example 1

Synthesis of Glucose-Triptolide Conjugates

Figures 1A, 1B:
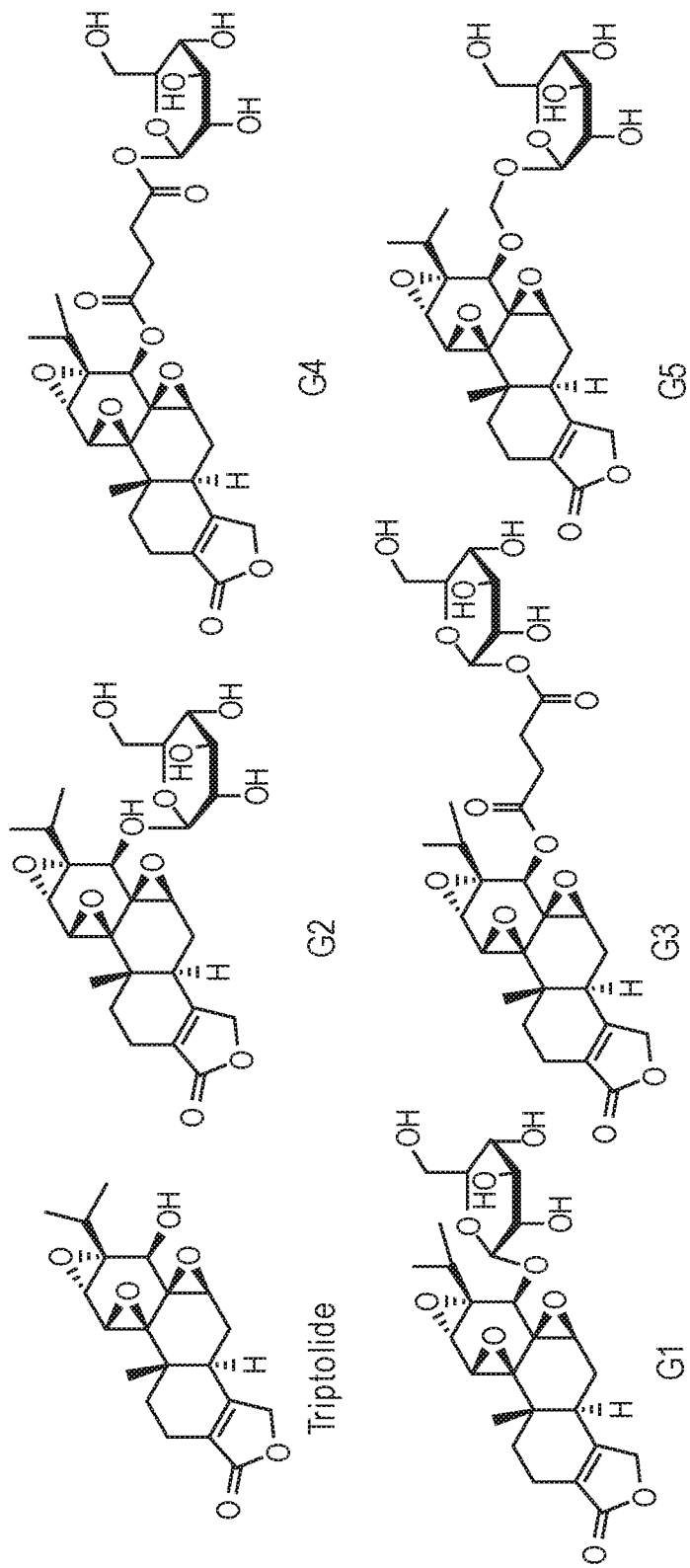
FIGS. 1A-1B. (a) The structure of triptolide and glucose conjugated analogs. (b) The octanol-water partition coefficient log P of different analogs using Interactive log P calculator.
Figure 2A:
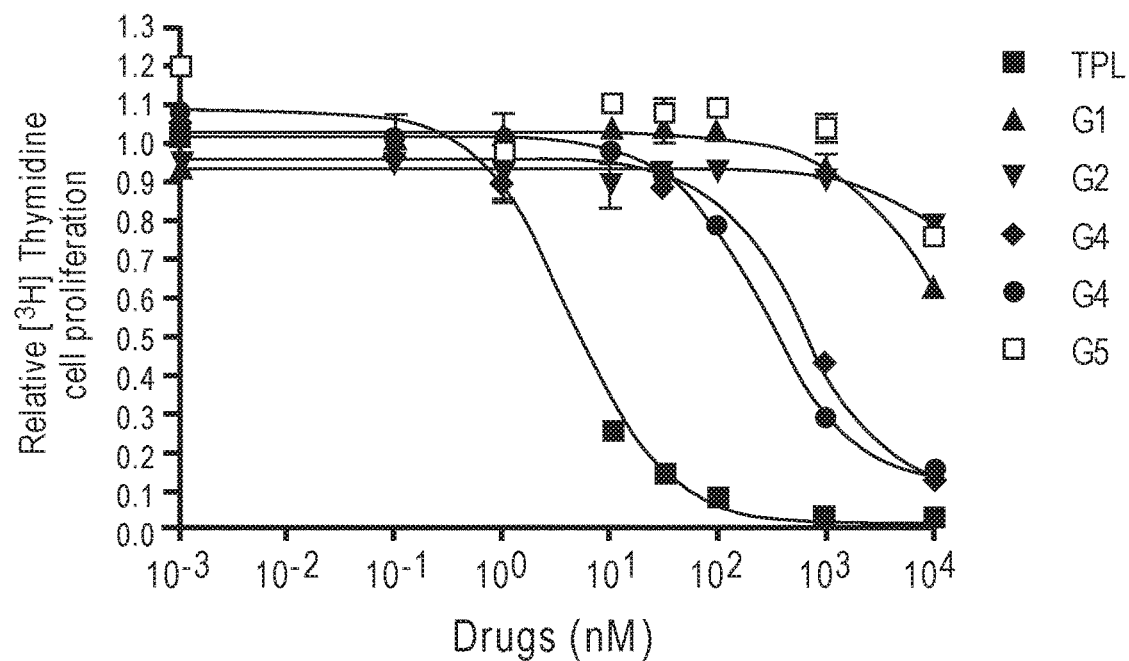
FIGS. 2A-2D. (a) Effects of G1-5 on HeLa cell proliferation. (b) Effects of G1-5 on ATPase activity of TFIIH in vitro. (c) Effects of G3 and G4 on the stability of RNAPII catalytic subunit. (d) Effects of G1, G2 and G5 on the stability of the RNAPII catalytic subunit.
Figure 2B:
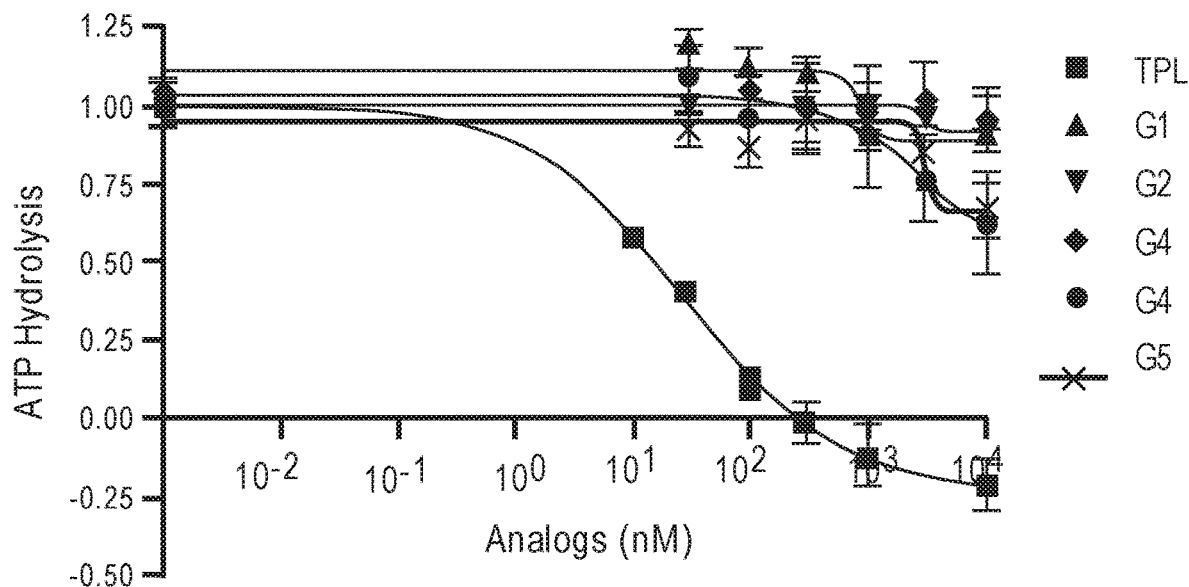
Figure 2C:
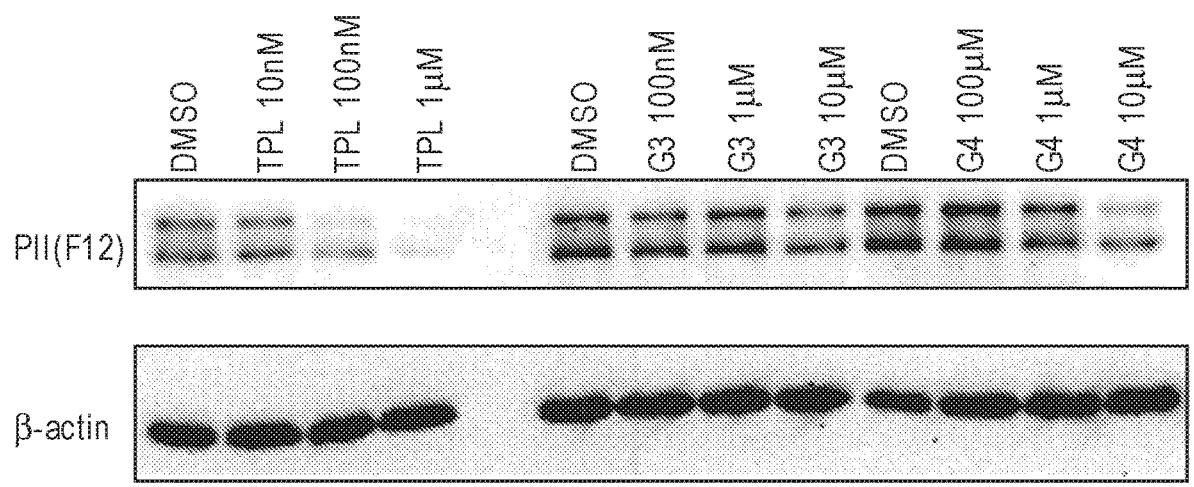
Figure 2D:
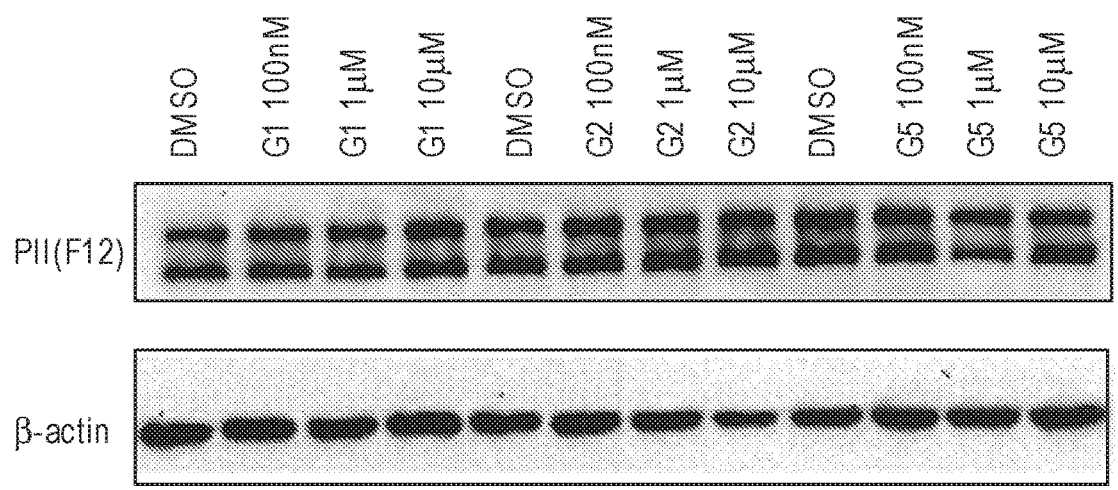

This example illustrates the synthesis of glucose-conjugated triptolide compounds. Five glucose conjugates with different types of linkers connecting glucose to triptolide were synthesized, designated G1-G5 (schemes I-III). Based on calculation, the Octanol-water partition coefficient, Log P, values were significantly improved over triptolide itself (FIG. 1).

Scheme I - The synthesis of glucose conjugated triptolide analogs G1 and G2.

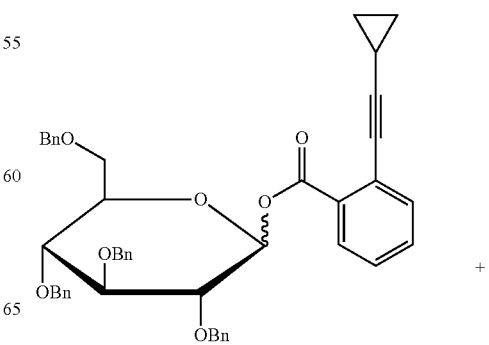

13
-continued
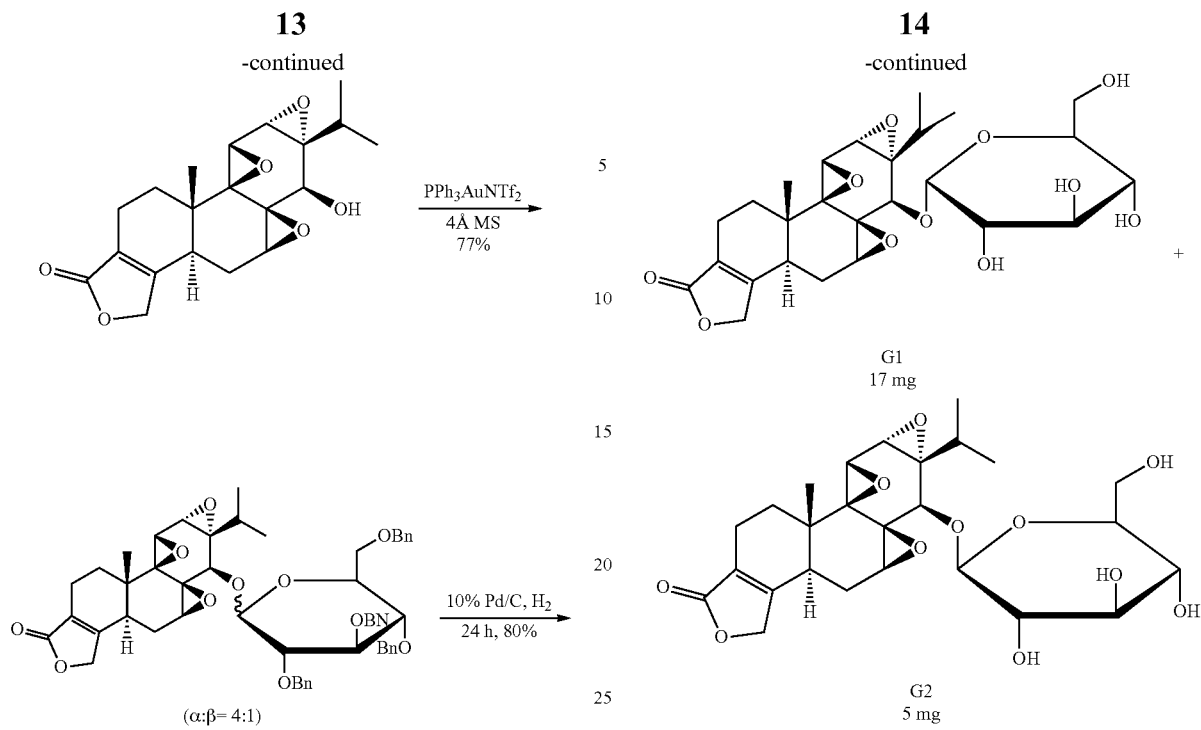
14
-continued
Scheme II - The synthesis of glucose conjugated triptolide analogs G3 and G4.
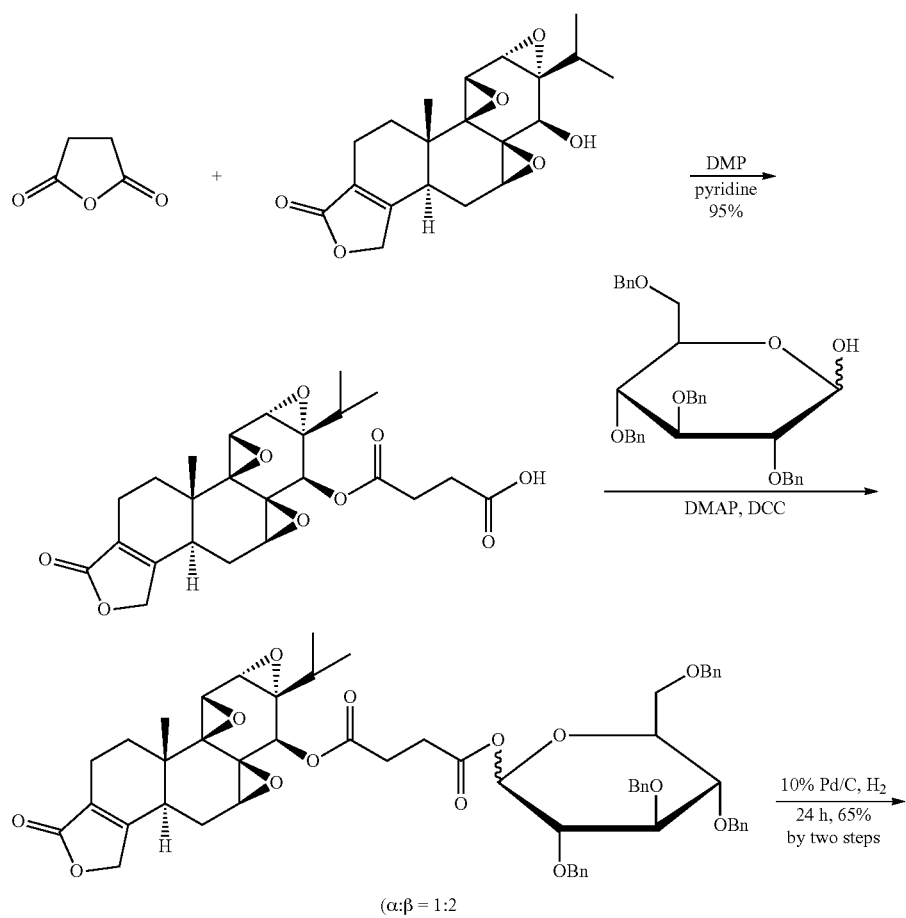

-continued
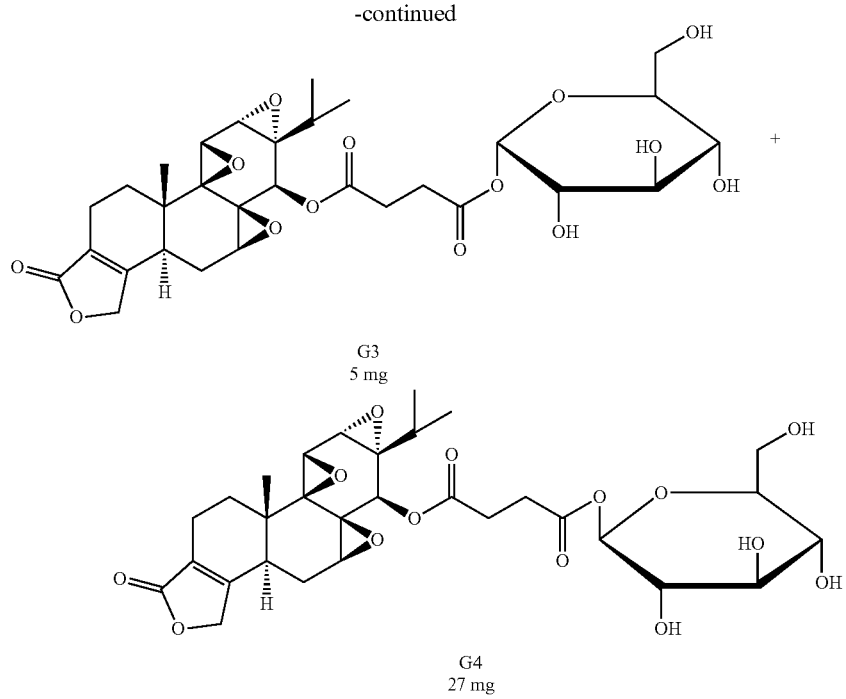
G3
5 mg
G4
27 mg
Scheme III - The synthesis of glucose conjugated triptolide analog G5.
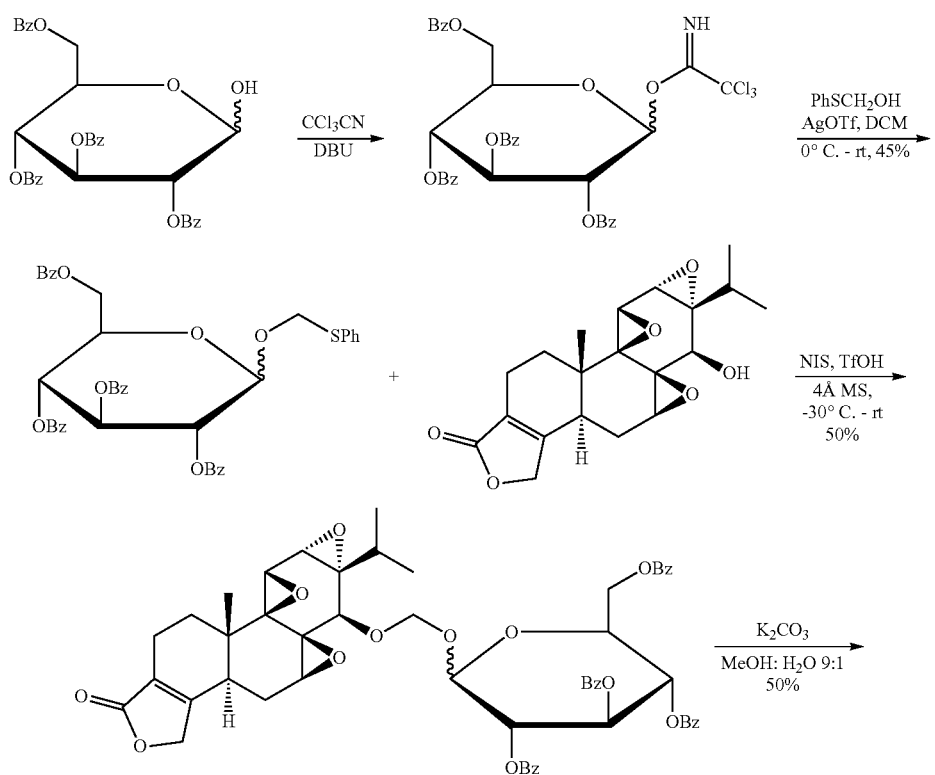

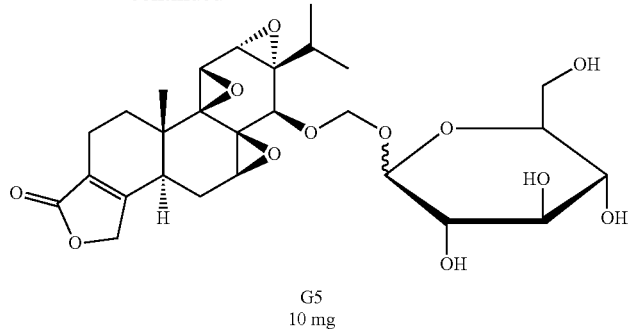

G5
10 mg

The activity of the different glucose-triptolide conjugates was assessed in vitro (FIG. 2). It was found that they differ in their anti-proliferative activity as measured by tritiated thymidine incorporation with G4 and G3 showing moderate activity, while G1, G2 and G5 exhibiting significantly reduced activity. The ability of the glucose conjugates to inhibit the ATPase activity of XPB in the TFIIH complex was also addressed. Interestingly, none of the five glucose conjugates showed appreciable inhibitory activity, suggesting that the cellular activity was a result of breakdown of the conjugates either in cell culture or upon entry into cells. Lastly, the ability of the glucose conjugates to cause degradation of the catalytic subunit of RNAPII was determined, an effect that has been previously observed for triptolide. In parallel with the antiproliferative activity, G4 was most active in inducing RNAPII catalytic subunit degradation with G3 showing weaker activity and the rest of the glucose conjugates showing little activity.

Example 2

In Vivo Activity of Glucose-Triptolide Conjugates

Figure 3:
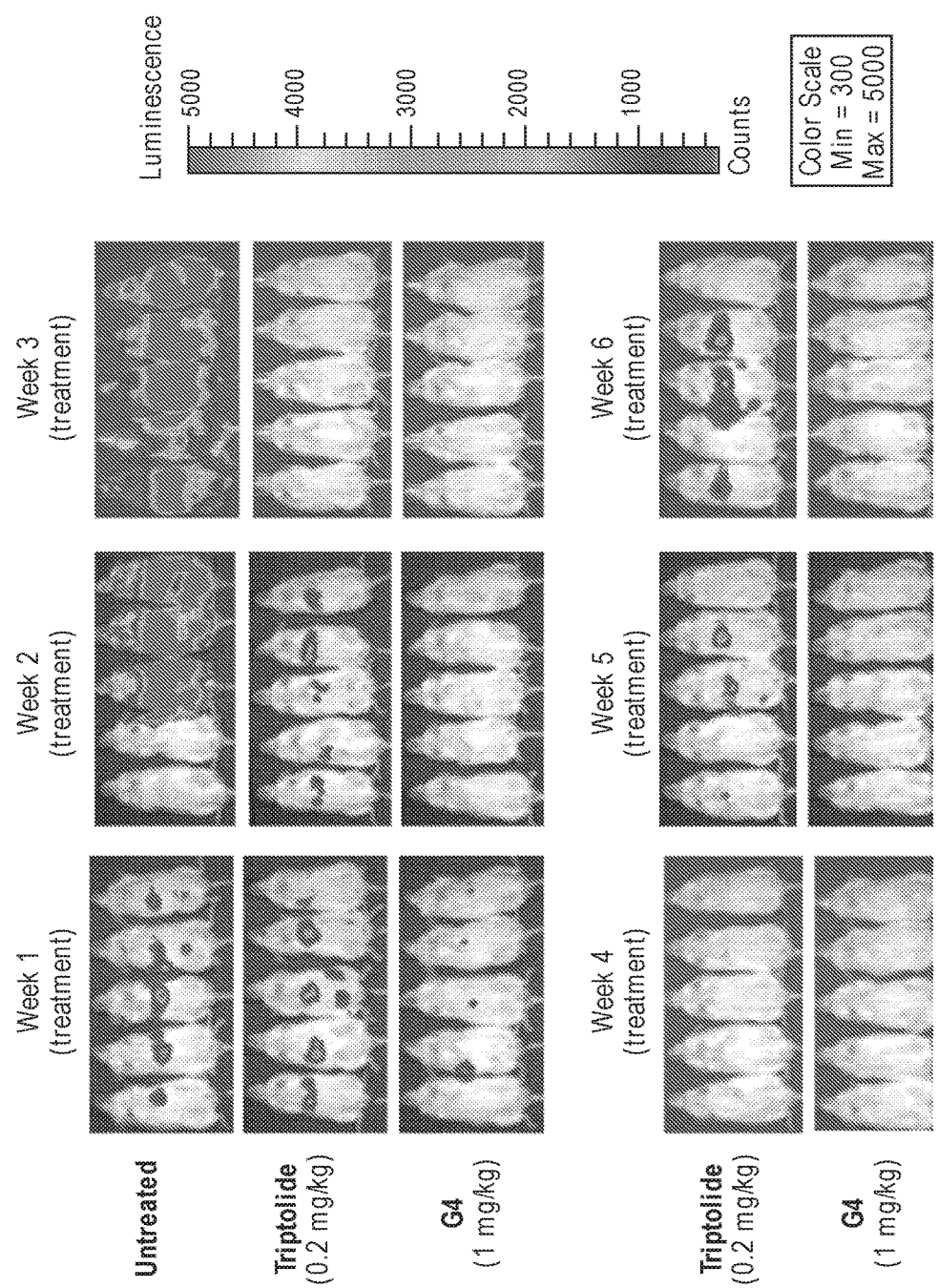
FIG. 3. Effects of triptolide and glucose-triptolide conjugate G4 in a metastatic mouse prostate cancer model. The injected prostate cancer cells expressed luciferase, which was detected by imaging of live animals.

The in vivo antitumor activity of the glucose-triptolide conjugate G4 was determined using an established metastatic prostate cancer model (Reference 1). In this model, the luciferase-expressing prostate cancer line PC3/ML was injected into NOD/SCID/IL2rγ$^{null}$ (NSG) mice through the tail vein. The metastasis of the injected prostate cancer cells into liver, kidney, lung and bone can be monitored in live animals by bioluminescent imaging (BLI). It was shown that this is a reliable model with reproducible liver metastasis and all animals succumb by Week 7 after injection of cells (or Week 4 after initiation of treatments). In preliminary experiments, it was found that the tolerable treatment dose of triptolide to be 0.2 mg/kg and that of G4 to be 1 mg/kg. Three weeks after cell injection, each compound was given once daily by IP at those doses for a total of 4 weeks. The surviving animals were continuously monitored upon termination of compound administration. As shown in FIG. 3, mice treated with 11 had lower tumor burden during Weeks 1 and 2 compared with those treated with triptolide. At the end of Week 4, both treatment groups showed undetectable tumor cells while all animals in the untreated groups died. Upon termination of compound administration, tumors immediately returned in animals treated with triptolide. But no tumor cells were detectable in those treated with G4 till the end of the experiment, revealing sustained anticancer activity of G4 in vivo.

Example 3

Other glucose triptolide conjugates with structures similar to Formulas G1-G5 are included in the present invention.

Such structures are represented by Formulas G6-G9, wherein R is a direct bond, substituted or unsubstituted —($C_1$-$C_6$)alkyl-, substituted or unsubstituted —$(CH_2)_n$O ($C_1$-$C_6$)alkyl-, substituted or unsubstituted —$(CH_2)_n$C(O)—, substituted or unsubstituted —$(CH_2)_n$C(O)($C_1$-$C_6$) alkyl-, substituted or unsubstituted —$(CH_2)_n$C(O)O($C_1$-$C_6$) alkyl-, substituted or unsubstituted —$(CH_2)_n$NH($C_1$-$C_6$) alkyl-, substituted or unsubstituted —$(CH_2)_n$C(O)NH($C_1$-$C_6$)alkyl-, substituted or unsubstituted —$(CH_2)_n$S($C_1$-$C_6$) alkyl-, substituted or unsubstituted —$(CH_2)_n$C(O)$(CH_2)_n$S ($C_1$-$C_6$)alkyl-, substituted or unsubstituted —($C_2$-$C_6$) alkenyl-, substituted or unsubstituted —$(CH_2)_n$O($C_2$-$C_6$) alkenyl-, substituted or unsubstituted —$(CH_2)_n$C(O)($C_2$-$C_6$) alkenyl-, substituted or unsubstituted —$(CH_2)_n$C(O)O($C_2$-$C_6$)alkenyl-, substituted or unsubstituted —$(CH_2)_n$NH($C_1$-$C_6$)alkenyl-, substituted or unsubstituted —($C_2$)$_n$C(O)NH ($C_2$-$C_6$)alkenyl-, substituted or unsubstituted —$(CH_2)_n$S ($C_2$-$C_6$)alkenyl-, substituted or unsubstituted $(CH_2)_n$C(O) $(CH_2)_n$S($C_2$-$C_6$)alkenyl-, substituted or unsubstituted —($C_2$—C)alkynyl-, substituted or unsubstituted —$(CH_2)_n$O ($C_2$-$C_6$)alkynyl-, substituted or unsubstituted —$(CH_2)_n$C(O) ($C_2$-$C_6$)alkynyl-, substituted or unsubstituted —$(CH_2)_n$C(O) O($C_2$-$C_6$)alkynyl-, substituted or unsubstituted —$(CH_2)_n$NH ($C_1$-$C_6$)alkynyl-, substituted or unsubstituted —$(CH_2)_n$C(O) NH($C_2$-$C_6$)alkynyl-, substituted or unsubstituted —$(CH_2)_n$S ($C_2$-$C_6$)alkynyl-, substituted or unsubstituted —$(CH_2)_n$C(O) $(CH_2)_n$S($C_2$-$C_6$)alkynyl-, wherein each alkyl, alkenyl and alkynyl group may be optionally substituted with alkyl, alkoxy, amino, carboxyl, cyano, nitro, or trifluoromethyl, wherein each n is independently an integer selected from 0, 1, 2, 3, 4, 5, and 6.

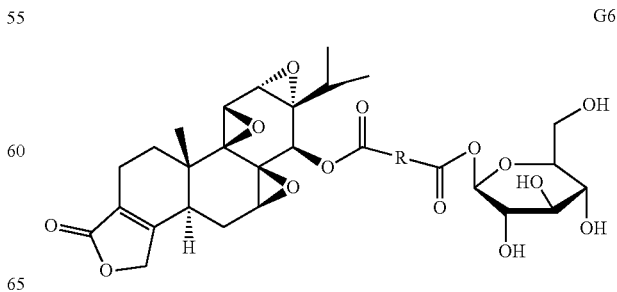

G6

G7
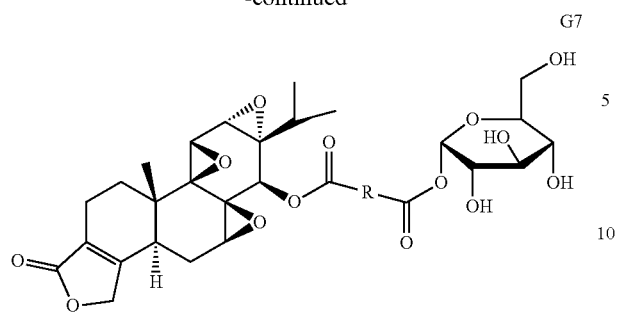
G8
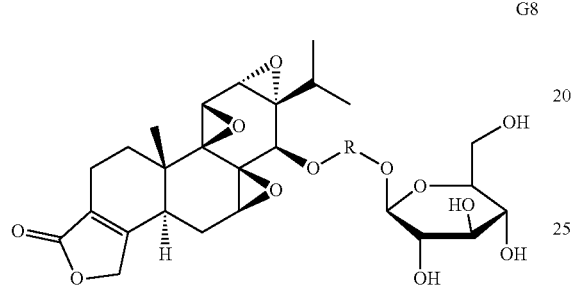
G9
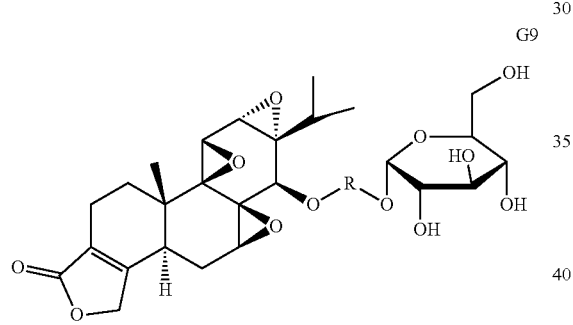
Example 4
Other glucose triptolide conjugates that are included in the present invention are compounds of Formula I:
T&A-L₁-Sugar    (I)
wherein the T&A moiety is triptolide or one of its analogs, and can be selected from compounds 1 to 18:
1
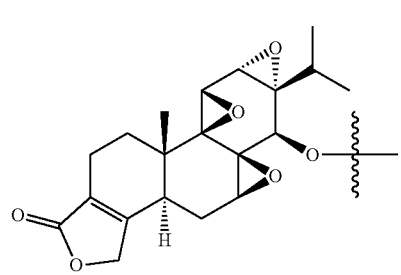
2
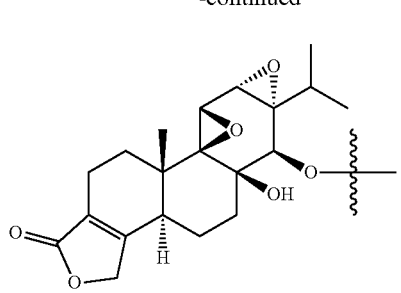
3
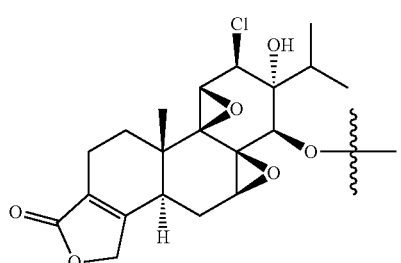
4, 5
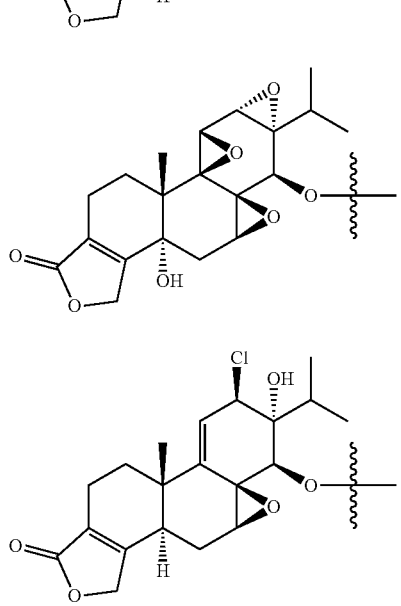
6
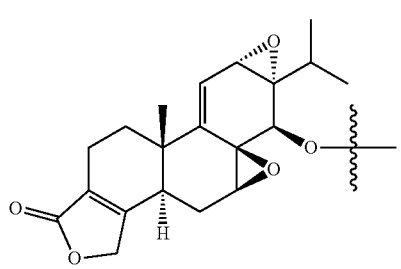
7
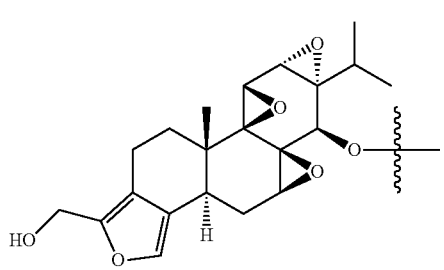

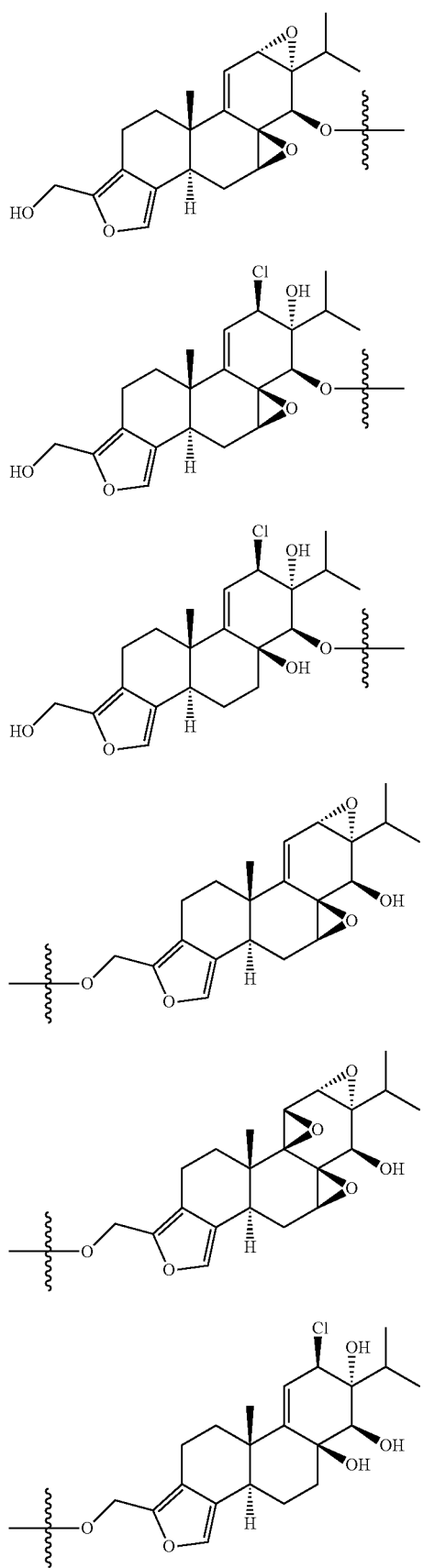
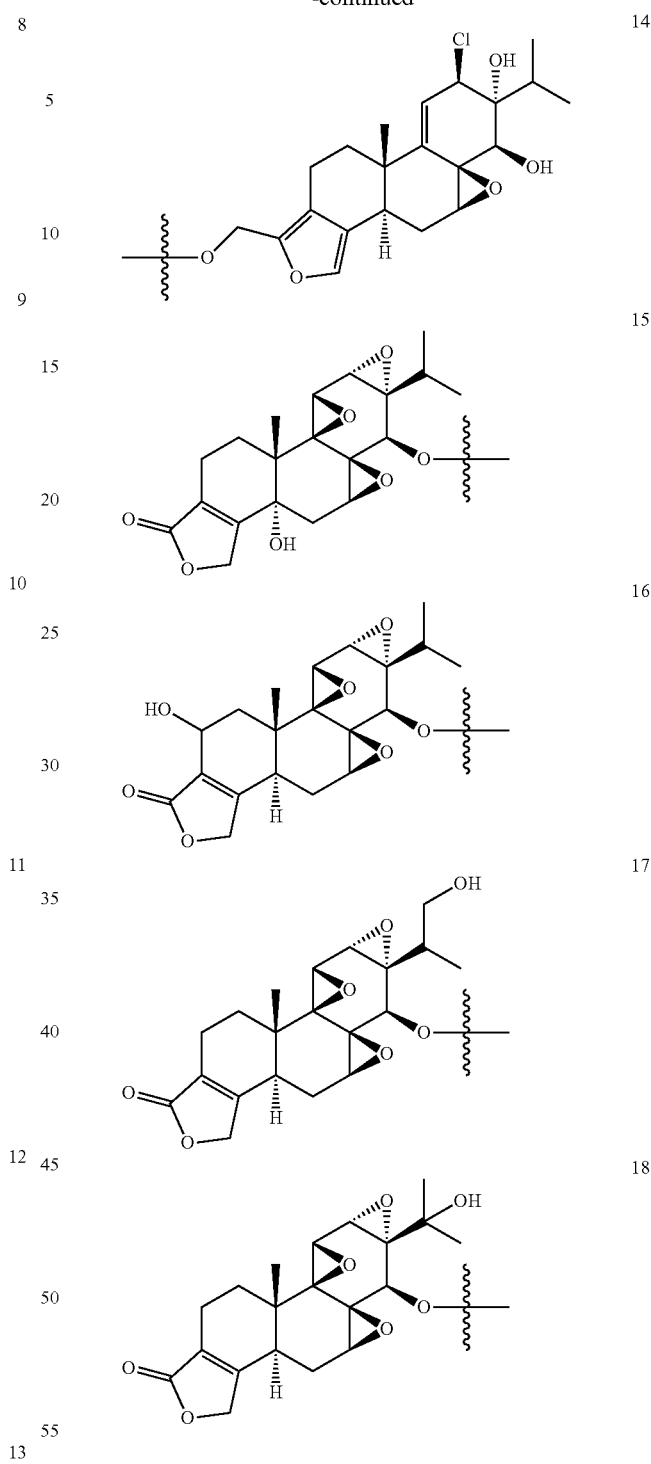

wherein $L_1$ can be selected from —X—Y—Z—, wherein X and Z can individually and independently be a direct bond, —$CH_2$—, —C(O)—, —SO—, —$SO_2$—, —OPO—, —$OPO_2$—; Y is a direct bond, a substituted or unsubstituted —($C_1$-$C_6$)alkyl-, substituted or unsubstituted —$(CH_2)_n$O($C_1$-$C_6$)alkyl-, substituted or unsubstituted —$(CH_2)_n$C(O)—, substituted or unsubstituted —$(CH_2)_n$C(O)($C_1$-$C_6$)alkyl-, substituted or unsubstituted —$(CH_2)_n$C(O)O($C_1$-$C_6$) alkyl-, substituted or unsubstituted —$(CH_2)_n$NH($C_1$-$C_6$) alkyl-, substituted or unsubstituted —$(CH_2)_n$C(O)NH($C_1$-$C_6$)alkyl-, substituted or unsubstituted —$(CH_2)_n$S($C_1$-$C_6$)

alkyl-, substituted or unsubstituted —(CH$_2$)$_n$C(O)(CH$_2$)$_n$S(C$_1$-C$_6$)alkyl-, substituted or unsubstituted —(C$_2$-C$_6$)alkenyl-, substituted or unsubstituted —(CH$_2$)$_n$O(C$_2$-C$_6$)alkenyl-, substituted or unsubstituted —(CH$_2$)$_n$C(O)(C$_2$-C$_6$)alkenyl-, substituted or unsubstituted —(CH$_2$)$_n$C(O)O(C$_2$-C$_6$)alkenyl-, substituted or unsubstituted —(CH$_2$)(O)NH(C$_1$-C$_6$)alkenyl-, substituted or unsubstituted —(CH$_2$)$_n$C(O)NH(C$_2$-C$_6$)alkenyl-, substituted or unsubstituted —(CH$_2$)$_n$S(C$_2$-C$_6$)alkenyl-, substituted or unsubstituted —(CH$_2$)$_n$C(O)(CH$_2$)$_n$S(C$_2$-C$_6$)alkenyl-, substituted or unsubstituted —(C$_2$-C$_6$)alkynyl-, substituted or unsubstituted —(CH$_2$)$_n$O(C$_2$-C$_6$)alkynyl-, substituted or unsubstituted —(CH$_2$)$_n$C(O)(C$_2$-C$_6$)alkynyl-, substituted or unsubstituted —(CH$_2$)$_n$C(O)O(C$_2$-C$_6$)alkynyl-, substituted or unsubstituted —(CH$_2$)$_n$NH(C$_1$-C$_6$)alkynyl-, substituted or unsubstituted —(CH$_2$)$_n$C(O)NH(C$_2$-C$_6$)alkynyl-, substituted or unsubstituted —(CH$_2$)$_n$S(C$_2$-C$_6$)alkynyl-, substituted or unsubstituted —(CH$_2$)$_n$C(O)(CH$_2$)$_n$S(C$_2$-C$_6$)alkynyl-, wherein each alkyl, alkenyl and alkynyl group may be optionally substituted with alkyl, alkoxy, amino, hydroxyl, oxo, aryl, heteroaryl, carboxyl, cyano, nitro, or trifluoromethyl;

wherein the sugar can be selected from compounds 19 to 53:

19

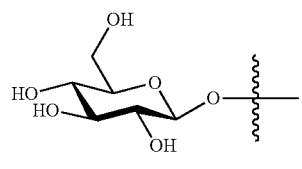

20

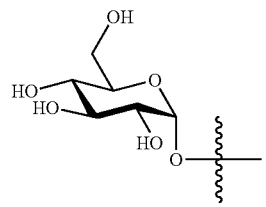

21

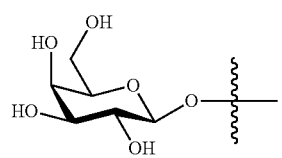

22

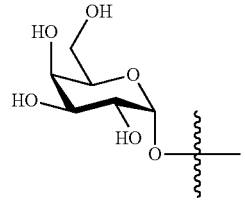

23

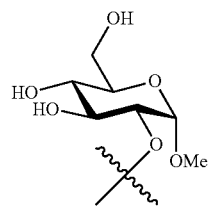

-continued

24

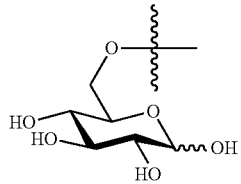

25

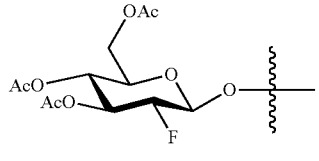

26

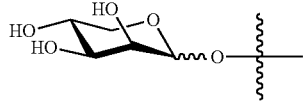

27

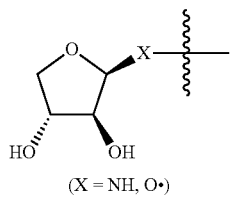

(X = NH, O•)

28

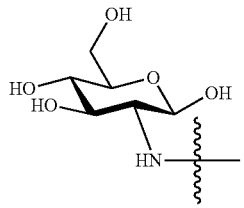

29

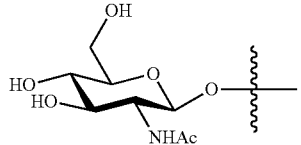

30

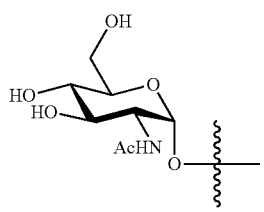

31

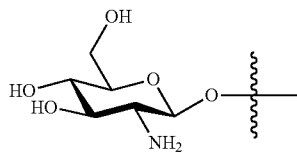

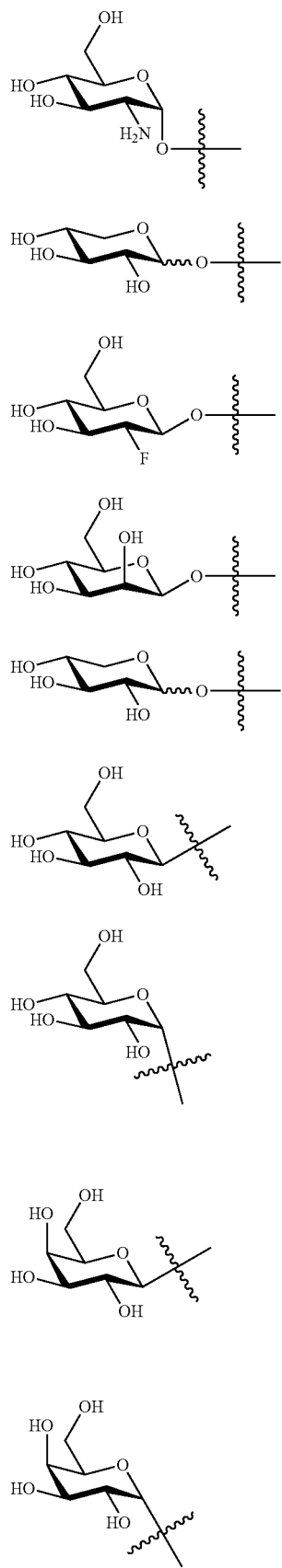
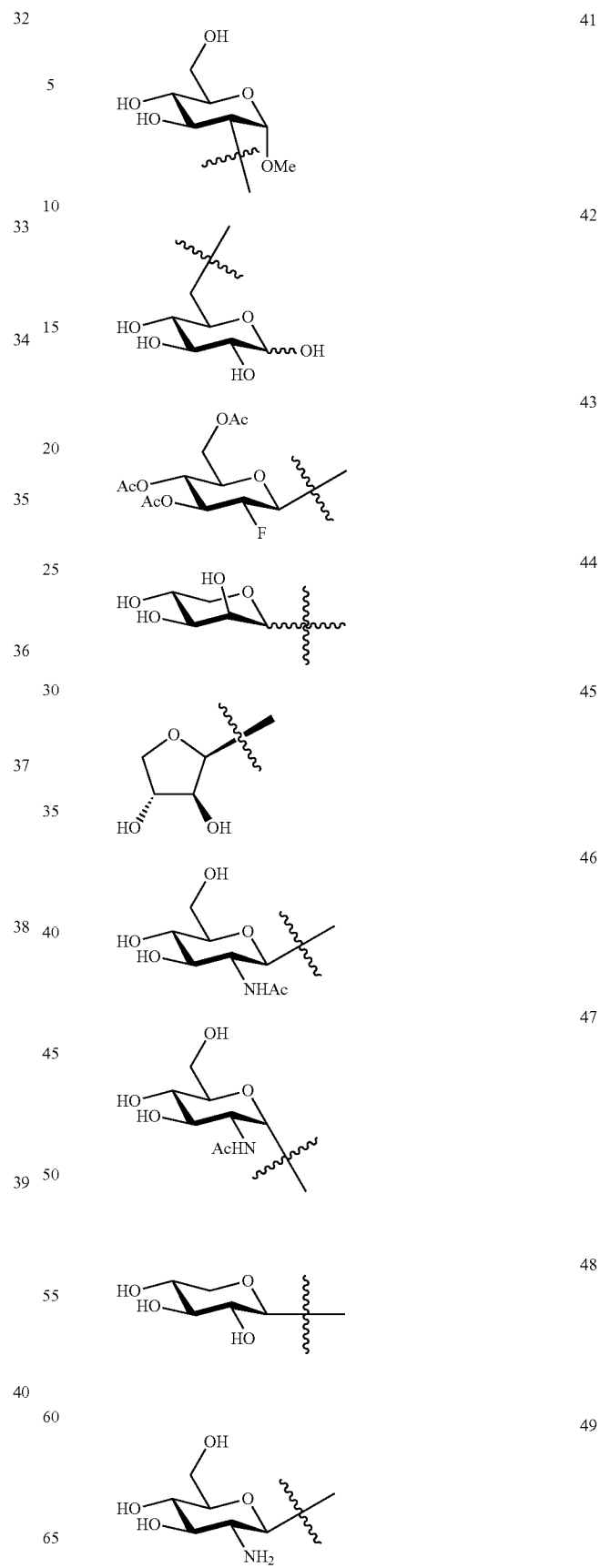

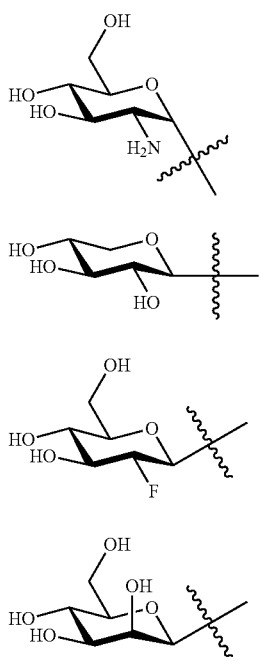

Although the invention has been described with reference to the above example, it will be understood that modifications and variations are encompassed within the spirit and scope of the invention. Accordingly, the invention is limited only by the following claims.

REFERENCES

The following reference is relied upon and incorporated herein in its entirety.

1. Bhatnagar A, Wang Y, Mease R C, Gabrielson M, Sysa P, Minn I, Green G, Simmons B, Gabrielson K, Sarkar S, Fisher P B, Pomper M G. AEG-1 promoter-mediated imaging of prostate cancer. Cancer Res. 2014; 74(20): 5772-81.

What is claimed is:

1. A compound of Formula I:

T&A-L$_1$-Sugar (I)

wherein the T&A moiety is triptolide or one of its analogs, and can be selected from compounds 1 to 18:

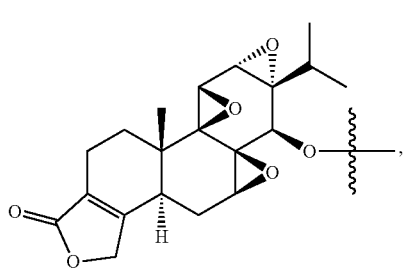

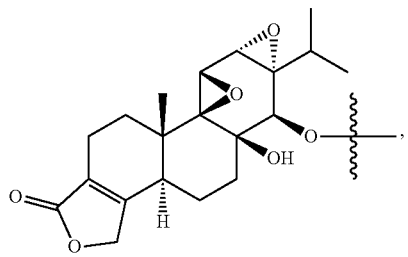

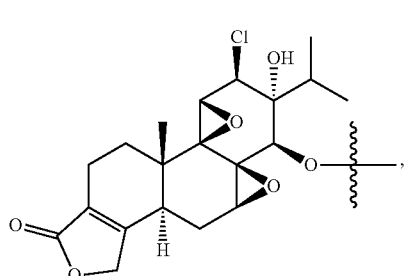

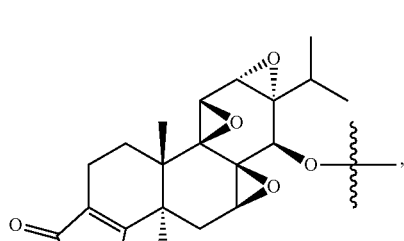

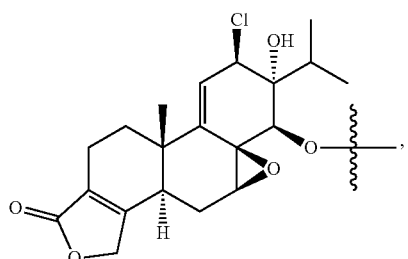

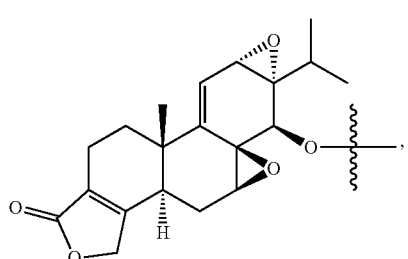

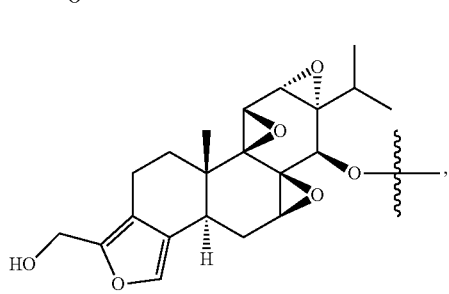

-continued

8
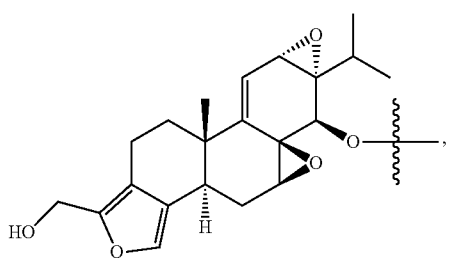

9
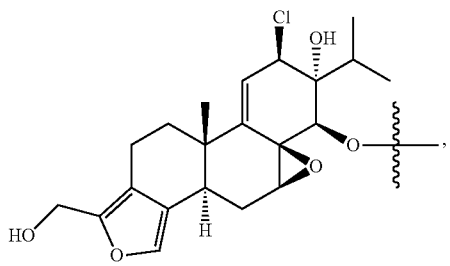

10
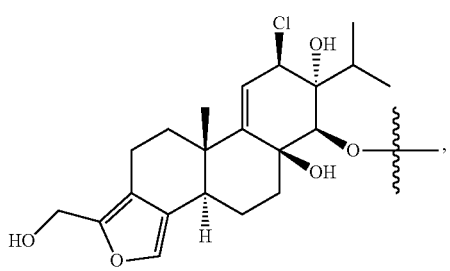

11
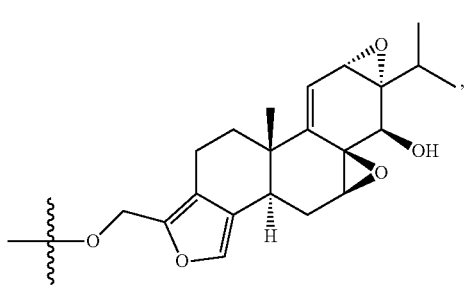

12
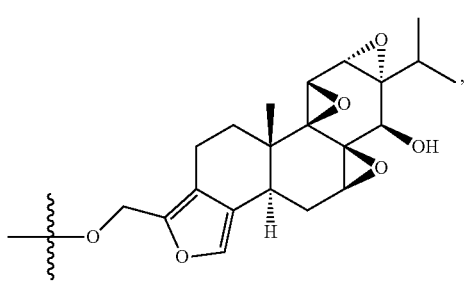

13
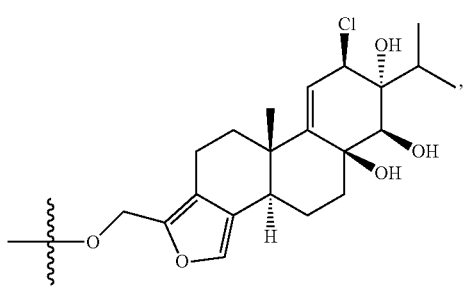

-continued

14
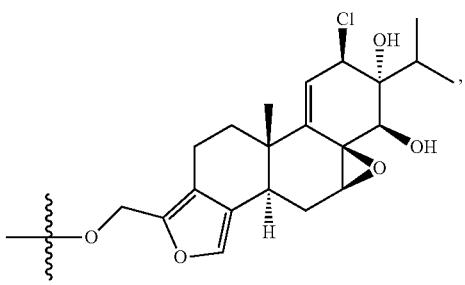

15
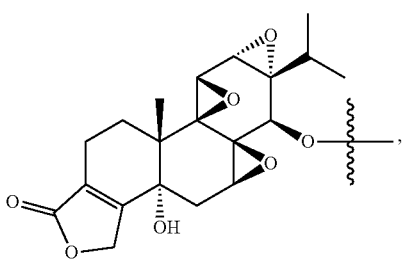

16
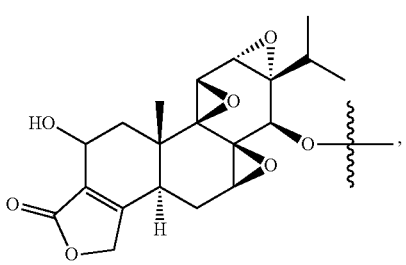

17
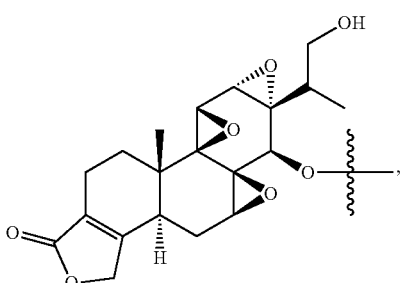

18
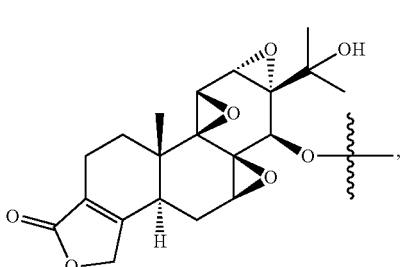

wherein $L_1$ can be selected from —X—Y—Z—, wherein X and Z can individually and independently be a direct bond, —CH$_2$—, —C(O)—, —SO—, —SO$_2$—, —OPO—, —OPO$_2$—, and wherein Y is a substituted or unsubstituted —(C$_1$-C$_6$)alkyl-, substituted or unsubstituted —(CH$_2$)$_n$O(C$_1$-C$_6$)alkyl-, substituted or unsubstituted —(CH$_2$)$_n$C(O)(C$_1$-C$_6$)alkyl-, substituted or unsubstituted —(CH$_2$)$_n$C(O)O(C$_1$-C$_6$)alkyl-, substituted or unsubstituted —(CH$_2$)$_n$NH(C$_1$-C$_6$)alkyl-, substituted or unsubstituted —(CH$_2$)$_n$C(O)NH(C$_1$-C$_6$)alkyl-, substituted or unsubstituted —(CH$_2$)$_n$S(C$_1$-C$_6$)

alkyl-, substituted or unsubstituted —(CH$_2$)$_n$C(O)(CH$_2$)$_n$S(C$_1$-C$_6$)alkyl-, substituted or unsubstituted —(C$_2$-C$_6$)alkenyl-, substituted or unsubstituted —(CH$_2$)$_n$O(C$_2$-C$_6$)alkenyl-, substituted or unsubstituted —(CH$_2$)$_n$C(O)(C$_2$-C$_6$)alkenyl-, substituted or unsubstituted —(CH$_2$)$_n$C(O)O(C$_2$-C$_6$)alkenyl-, substituted or unsubstituted —(CH$_2$)$_n$NH(C$_2$-C$_6$)alkenyl-, substituted or unsubstituted —(CH$_2$)$_n$C(O)NH(C$_2$-C$_6$)alkenyl-, substituted or unsubstituted —(CH$_2$)$_n$S(C$_2$-C$_6$)alkenyl-, substituted or unsubstituted —(CH$_2$)$_n$C(O)(CH$_2$)$_n$S(C$_2$-C$_6$)alkenyl-, substituted or unsubstituted —(C$_2$-C$_6$)alkynyl-, substituted or unsubstituted —(CH$_2$)$_n$O(C$_2$-C$_6$)alkynyl-, substituted or unsubstituted —(CH$_2$)$_n$C(O)(C$_2$-C$_6$)alkynyl-, substituted or unsubstituted —(CH$_2$)$_n$C(O)O(C$_2$-C$_6$)alkynyl-, substituted or unsubstituted —(CH$_2$)$_n$NH(C$_2$-C$_6$)alkynyl-, substituted or unsubstituted —(CH$_2$)$_n$C(O)NH(C$_2$-C$_6$)alkynyl-, substituted or unsubstituted —(CH$_2$)$_n$S(C$_2$-C$_6$)alkynyl-, substituted or unsubstituted —(CH$_2$)$_n$C(O)(CH$_2$)$_n$S(C$_2$-C$_6$)alkynyl-, wherein each alkyl, alkenyl and alkynyl group may be optionally substituted with alkyl, alkoxy, amino, hydroxyl, oxo, aryl, heteroaryl, carboxyl, cyano, nitro, or trifluoromethyl;

wherein n is an integer independently selected from 0, 1, 2, 3 4, 5, and 6;

wherein the sugar can be selected from compounds 19 to 30, 33 to 48, and 51 to 53:

19

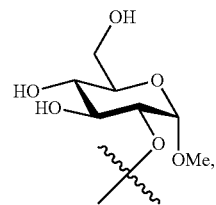

20

21

22

23

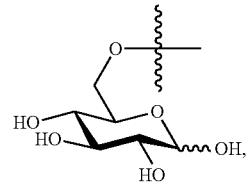

24

25

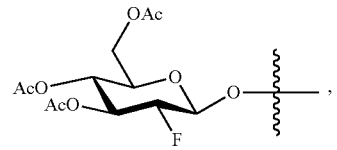

26

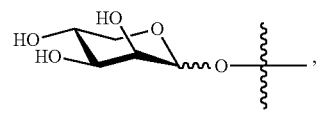

27

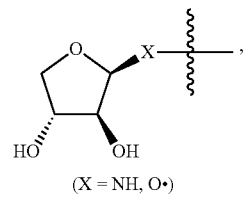

(X = NH, O•)

28

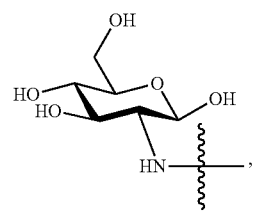

29

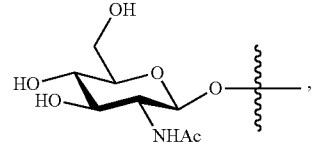

30

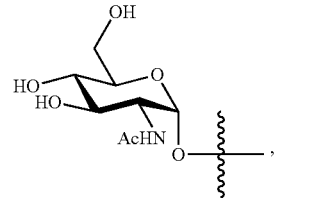

33

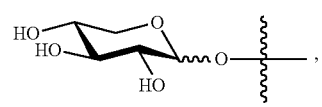

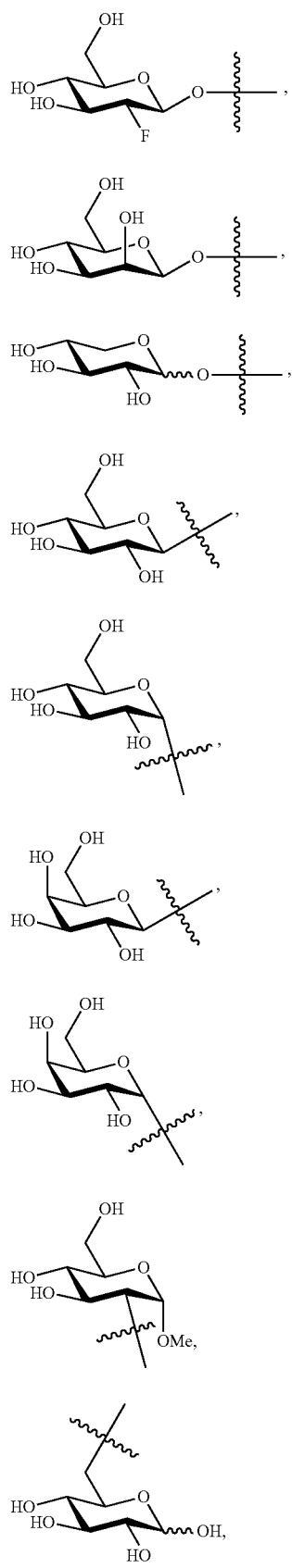

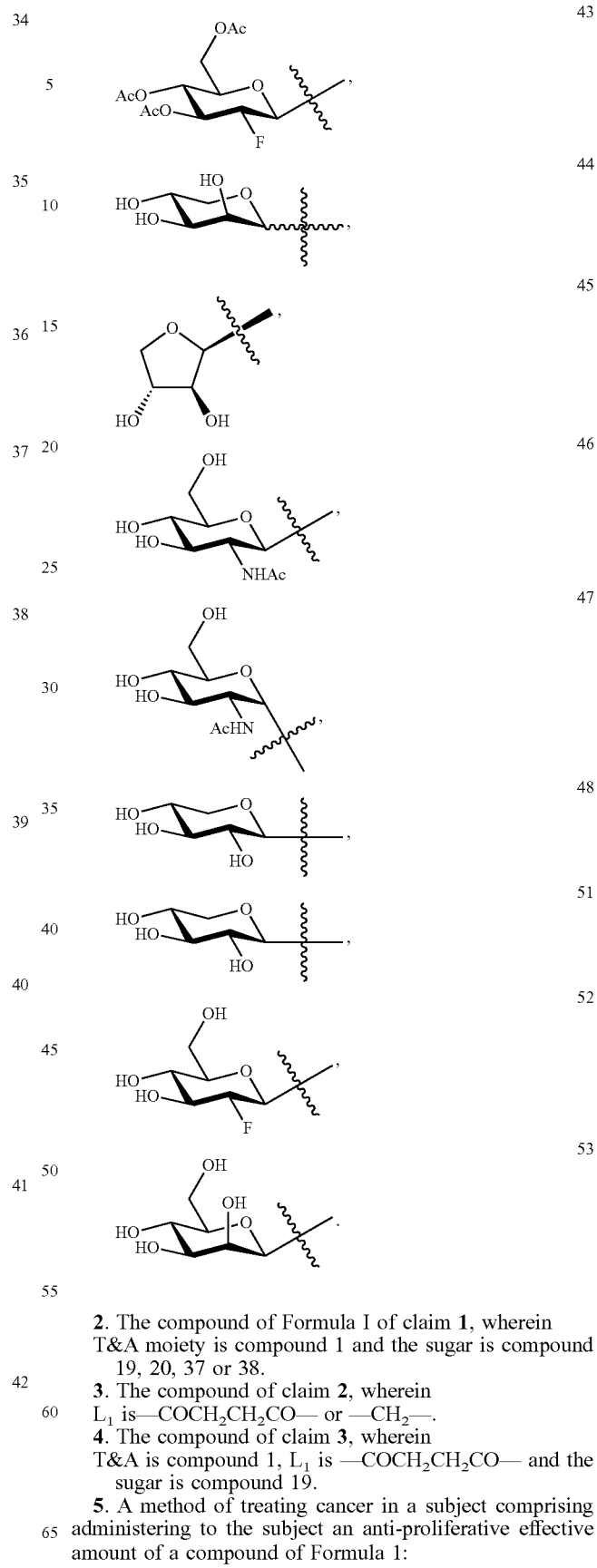

2. The compound of Formula I of claim 1, wherein T&A moiety is compound 1 and the sugar is compound 19, 20, 37 or 38.

3. The compound of claim 2, wherein
L$_1$ is —COCH$_2$CH$_2$CO— or —CH$_2$—.

4. The compound of claim 3, wherein
T&A is compound 1, L$_1$ is —COCH$_2$CH$_2$CO— and the sugar is compound 19.

5. A method of treating cancer in a subject comprising administering to the subject an anti-proliferative effective amount of a compound of Formula 1:

$$T\&A-L_1-Sugar \qquad (I)$$

wherein the T&A moiety is triptolide or one of its analogs, and can be selected from compounds 1 to 18:
1
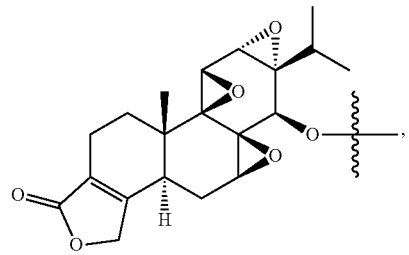
2
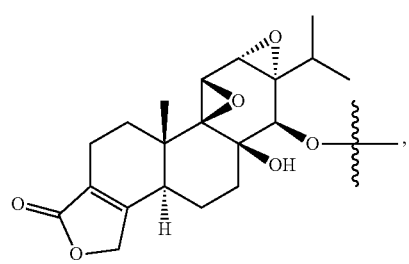
3
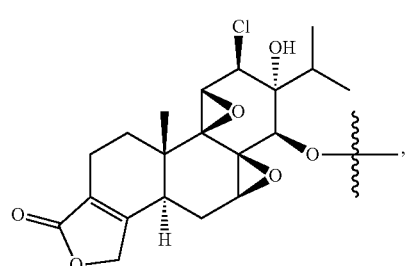
4
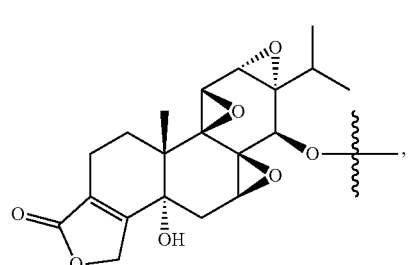
5
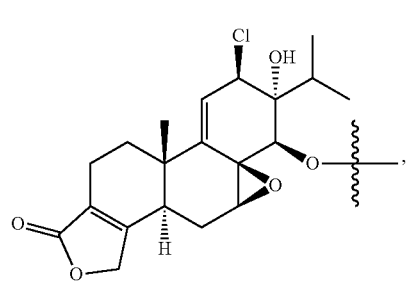
-continued
6
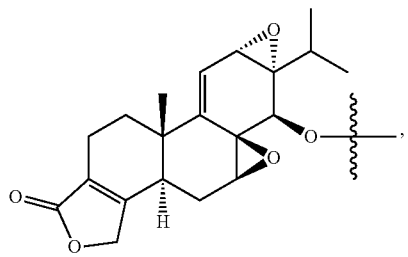
7
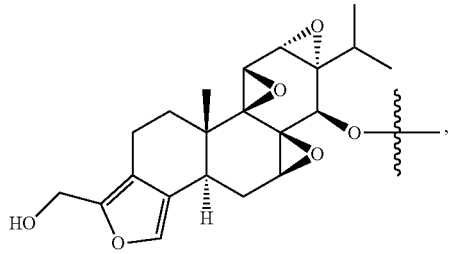
8
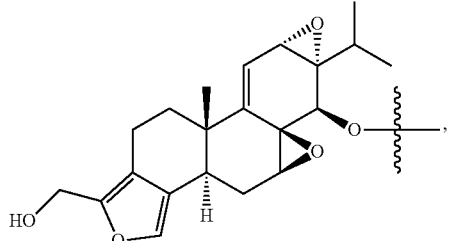
9
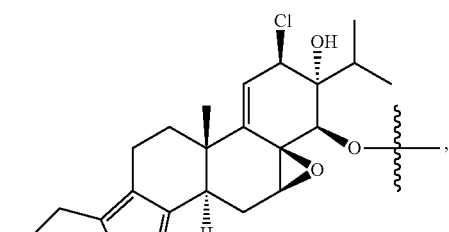
10
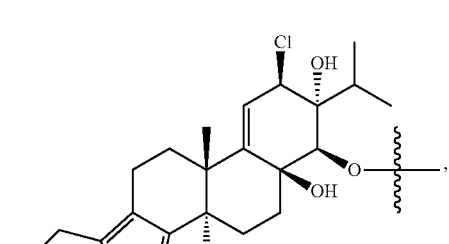
11
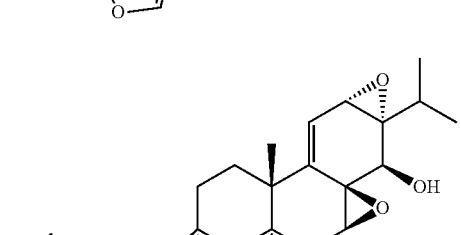
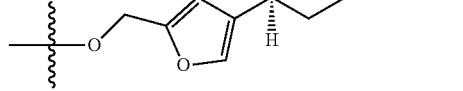

37
-continued

12
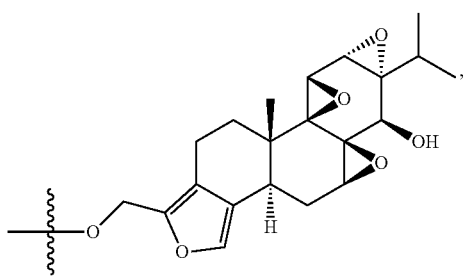

13
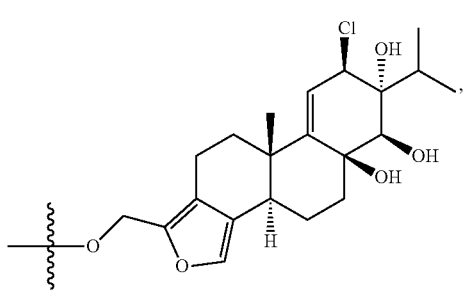

14
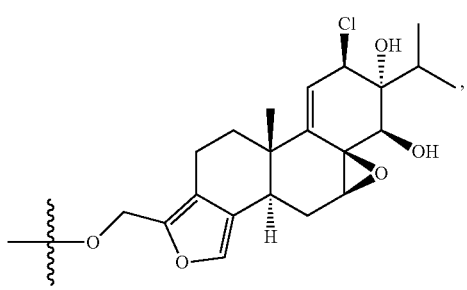

15
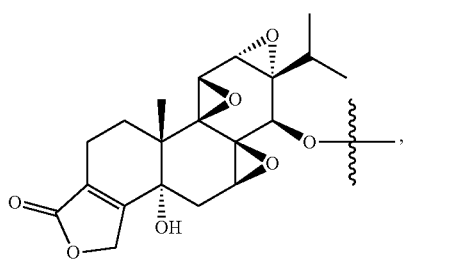

16
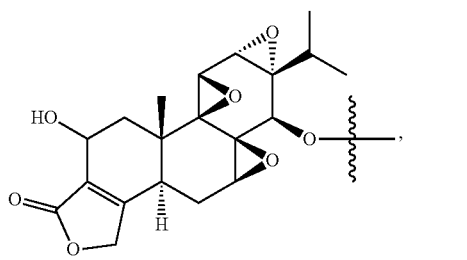

38
-continued

17
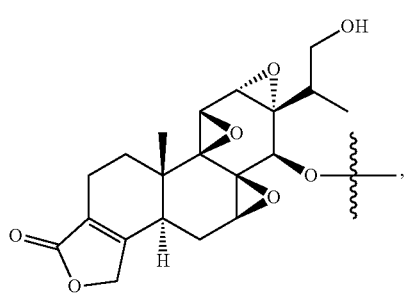

18
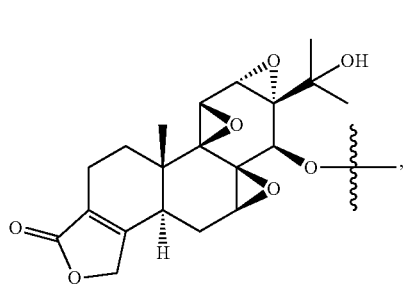

wherein $L_1$ can be selected from —X—Y—Z—, wherein X and Z can individually and independently be a direct bond, —$CH_2$—, —C(O)—, —SO—, —$SO_2$—, —OPO—, —$OPO_2$—, and wherein Y is a substituted or unsubstituted —($C_1$-$C_6$)alkyl-, substituted or unsubstituted —$(CH_2)_nO(C_1$-$C_6)$alkyl-, substituted or unsubstituted —$(CH_2)_nC(O)(C_1$-$C_6)$alkyl-, substituted or unsubstituted —$(CH_2)_nC(O)O(C_1$-$C_6)$alkyl-, substituted or unsubstituted —$(CH_2)_nNH(C_1$-$C_6)$alkyl-, substituted or unsubstituted —$(CH_2)_nC(O)NH(C_1$-$C_6)$alkyl-, substituted or unsubstituted —$(CH_2)_nS(C_1$-$C_6)$alkyl-, substituted or unsubstituted —$(CH_2)_nC(O)(CH_2)_nS(C_1$-$C_6)$alkyl-, substituted or unsubstituted —($C_2$-$C_6$)alkenyl-, substituted or unsubstituted —$(CH_2)_nO(C_2$-$C_6)$alkenyl-, substituted or unsubstituted —$(CH_2)_nC(O)(C_2$-$C_6)$alkenyl-, substituted or unsubstituted —$(CH_2)_nC(O)O(C_2$-$C_6)$alkenyl-, substituted or unsubstituted —$(CH_2)_nNH(C_2$-$C_6)$alkenyl-, substituted or unsubstituted —$(CH_2)_nC(O)NH(C_2$-$C_6)$alkenyl-, substituted or unsubstituted —$(CH_2)_nS(C_2$-$C_6)$alkenyl-, substituted or unsubstituted —$(CH_2)_nC(O)(CH_2)_nS(C_2$-$C_6)$alkenyl-, substituted or unsubstituted —($C_2$-$C_6$)alkynyl-, substituted or unsubstituted —$(CH_2)_nO(C_2$-$C_6)$alkynyl-, substituted or unsubstituted —$(CH_2)_nC(O)(C_2$-$C_6)$alkynyl-, substituted or unsubstituted —$(CH_2)_nC(O)O(C_2$-$C_6)$alkynyl-, substituted or unsubstituted —$(CH_2)_nNH(C_2$-$C_6)$alkynyl-, substituted or unsubstituted —$(CH_2)_nC(O)NH(C_2$-$C_6)$alkynyl-, substituted or unsubstituted —$(CH_2)_nS(C_2$-$C_6)$alkynyl-, substituted or unsubstituted —$(CH_2)_nC(O)(CH_2)_nS(C_2$-$C_6)$alkynyl-, wherein each alkyl, alkenyl and alkynyl group may be optionally substituted with alkyl, alkoxy, amino, hydroxyl, oxo, aryl, heteroaryl, carboxyl, cyano, nitro, or trifluoromethyl;

wherein n is an integer independently selected from 0, 1, 2, 3 4, 5, and 6;

wherein the sugar can be selected from compounds 19 to 30, 33 to 48, and 51 to 53:

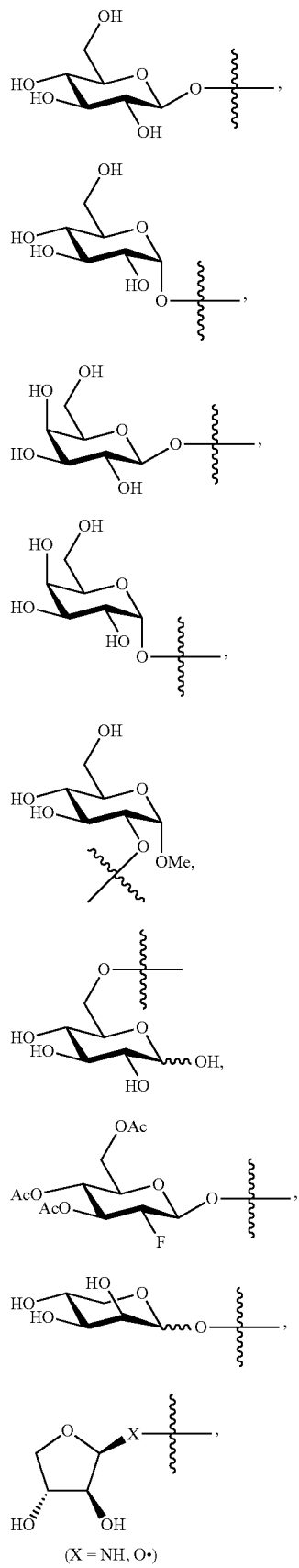

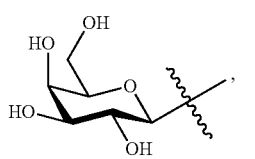

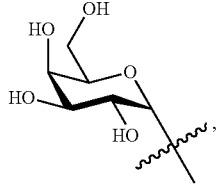

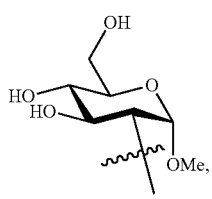

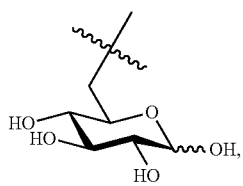

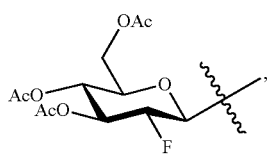

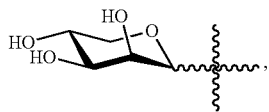

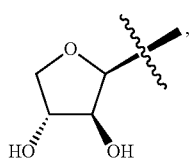

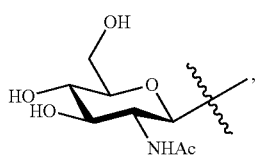

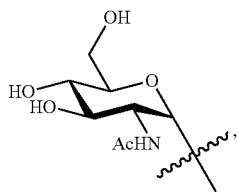

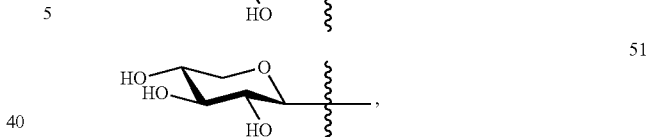

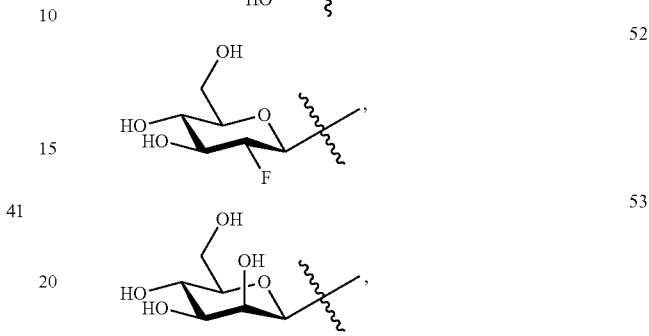

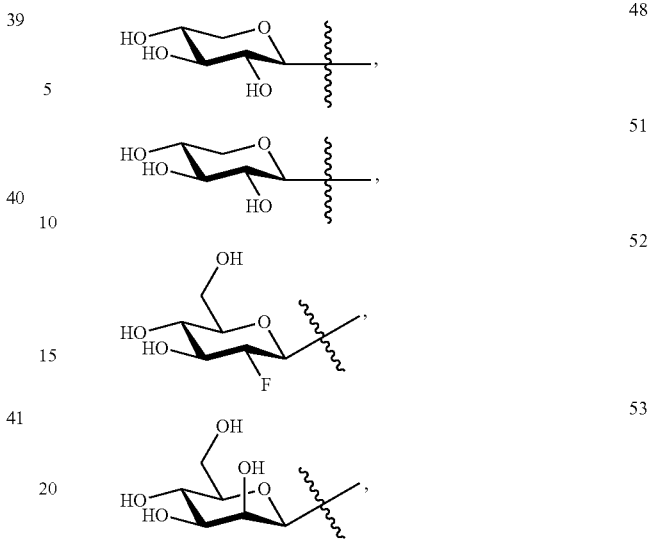

hereby treating the cancer.

6. The method of claim 5, wherein the compound is a compound of claim 2.

7. The method of claim 5, wherein the compound is a compound of claim 3.

8. The method of claim 5, wherein the compound is a compound of claim 4.

9. The method of claim 5, wherein the cancer is selected from the group consisting of bladder cancer, breast cancer, ovarian cancer, pancreatic cancer, and gastric cancer, cervical cancer, colon cancer, endometrial cancer, head and neck cancer, lung cancer, melanoma, multiple myeloma, leukemia, non-hodgkin's lymphoma, prostate cancer, rectal cancer, malignant melanomas, alimentary/gastrointestinal tract cancer, liver cancer, skin cancer, lymphoma, kidney cancer, muscle cancer, bone cancer, brain cancer, eye or ocular cancer, rectal cancer, colon cancer, cervical cancer, bladder cancer, oral cancer, benign and malignant tumors, stomach cancer, corpus uteri, testicular cancer, renal cancer, throat cancer, acute lymphocytic leukemia, acute myelogenous leukemia, Ewing's Sarcoma, Kaposi's Sarcoma, basal cell carinoma and squamous cell carcinoma, small cell lung cancer, choriocarcinoma, rhabdomyosarcoma, angiosarcoma, hemangioendothelioma, Wilms Tumor, neuroblastoma, mouth/pharynx cancer, esophageal cancer, larynx cancer, neurofibromatosis, tuberous sclerosis, hemangiomas, and lymphangiogenesis.

10. The method of claim 9, wherein the cancer is prostate cancer.

11. The method of claim 9, wherein the cancer is metastatic cancer.

12. The method of claim 9, wherein the compound is administered intravenously.

13. The method of claim 12, further comprising administering a chemotherapeutic compound.

14. A pharmaceutical composition comprising a compound of claim 3.

15. A method of treating possible organ rejection in a subject receiving an organ transplant comprising administering to the subject an anti-proliferative effective amount of a glucose-triptolide conjugate compound, thereby treating the possible organ rejection.

16. The method of claim 15, wherein the compound is a compound of claim 1.

17. The method of claim 15, wherein the compound is a compound of claim 2.

18. The method of claim 15, wherein the compound is a compound of claim 3.

19. The method of claim 15, wherein the compound is a compound of claim 4.

20. The method of claim 15, wherein the compound is administered intravenously.

21. A method of treating an autoimmune disease in a subject comprising administering to the subject an anti-proliferative effective amount of a glucose-triptolide conjugate compound, thereby treating the autoimmune disease.

22. The method of claim 21, wherein the compound is a compound of claim 1.

23. The method of claim 21, wherein the compound is a compound of claim 2.

24. The method of claim 21, wherein the compound is a compound of claim 3.

25. The method of claim 21, wherein the compound is a compound of claim 4.

26. The method of claim 21, wherein the autoimmune disease is selected from the group consisting of Acute disseminated encephalomyelitis (ADEM), Addison's disease, Ankylosing spondylitis, Antiphospholipid antibody syndrome, Autoimmune hemolytic anemia, Autoimmune hepatitis, Autoimmune inner ear disease, Autoimmune Lymphoproliferative Syndrome (ALPS), Autoimmune polyendocrine/polyglandular syndrome, Autoimmune thrombocytoipenia purpura, Balo disease, Behçet disease, Bullous pemphigoid, Cardiomyopathy, Celiac sprue-dermatitis herpetiformis, Chronic fatigue immune dysfunction syndrome (CFIDS), Chronic inflammatory demyelinating neuropathy, Cicatrical pemphigoid, Coeliac disease, Cold agglutinin disease, CREST syndrome, Crohn's disease, Cystic fibrosis, Degos disease, Dermatomyositis, Diabetes (Type I or Juvenile onset), Early onset dementia, Eczema, Endotoxin shock, Essential mixed cryoglobulinemia, Familial Mediterranean fever, Fibromyalgia, Fibromyositis, Goodpasture's syndrome, Graves' disease, Guillain-Barré syndrome (GBS), Hashimoto's thyroidosis, Hidradenitis suppurativa, Idiopathic pulmonary fibrosis, Idiopathic thrombocytopenic purpura, IgA nephropathy, Lambert-Eaton Myasthenic Syndrome, Leukemia, Lichen planus, Ménière disease, Mixed connective tissue disease, Multiple sclerosis, Multiphasic disseminated encephalomyelitis, Myasthenia gravis, Neuromyelitis Optica, Paraneoplastic Syndromes, Pemphigus, Pemphigus vulgaris, Pernicious anaemia, Polyarteritis nodosum, Polychondritis, Polymyalgia rhematica, Polymyositis, Primary agammaglobulinemia, Primary biliary cirrhosis, Plaque Psoriasis, Psoriatic arthritis, Raynaud phenomenon, Reiter syndrome, Restenosis following angioplasty, Rheumatic fever, Rheumatoid arthritis, Rheumatoid psoriasis, Sarcoidosis, Scleroderma, Sepsis, Sezary's disease, Sjögren's syndrome, Stiff-person syndrome, Lupus including Systemic lupus erythematosis (SLE), Takayasu arteritis, Temporal arteritis (also known as "giant cell arteritis"), Transplant or Allograft rejection, Ulcerative colitis, Uveitis, Vasculitis, Vitiligo, Graft vs Host disease, pustular psoriasis, and Wegener's granulomatosis (now termed Granulomatosis with Polyangiitis (GPA), inflammatory bowel disease, Acute necrotizing hemorrhagic leukoencephalitis, Agammaglobulinemia, Alopecia areata, Amyloidosis, Anti-GBM/Anti-TBM nephritis, Antiphospholipid syndrome (APS), Autoimmune angioedema, Autoimmune aplastic anemia, Autoimmune dysautonomia, Autoimmune hyperlipidemia, Autoimmune immunodeficiency, Autoimmune inner ear disease (AIED), Autoimmune myocarditis, Autoimmune oophoritis, Autoimmune pancreatitis, Autoimmune retinopathy, Autoimmune thyroid disease, Autoimmune urticarial, Axonal & neuronal neuropathies, Castleman disease, Celiac disease, Chagas disease, Chronic fatigue syndrome, Chronic inflammatory demyelinating polyneuropathy (CIDP), Chronic recurrent multifocal ostomyelitis (CRMO), Churg-Strauss syndrome, Cicatricial pemphigoid/benign mucosal pemphigoid, Cogans syndrome, Congenital heart block, Coxsackie myocarditis, CREST disease, Demyelinating neuropathies, Dermatitis herpetiformis, Devic's disease (neuromyelitis optica), Discoid lupus, Dressler's syndrome, Endometriosis, Eosinophilic esophagitis, Eosinophilic fasciitis, Erythema nodosum, Experimental allergic encephalomyelitis, Evans syndrome, Fibrosing alveolitis, Giant cell arteritis (temporal arteritis), Giant cell myocarditis, Glomerulonephritis, Granulomatosis with Polyangiitis (GPA) (formerly called Wegener's Granulomatosis), Hashimoto's encephalitis, Hashimoto's thyroiditis, Hemolytic anemia, Henoch-Schonlein purpura, Herpes gestationis, Hypogammaglobulinemia, Idiopathic thrombocytopenic purpura (ITP), IgG4-related sclerosing disease, Immunoregulatory lipoproteins, Inclusion body myositis, Interstitial cystitis, Juvenile arthritis, Juvenile diabetes (Type 1 diabetes), Juvenile myositis, Kawasaki syndrome, Lambert-Eaton syndrome, Leukocytoclastic vasculitis, Lichen sclerosus, Ligneous conjunctivitis, Linear IgA disease (LAD), Lupus (SLE), Lyme disease, chronic, Microscopic polyangiitis, Mooren's ulcer, Mucha-Habermann disease, Myositis, Narcolepsy, Neutropenia, Ocular cicatricial pemphigoid, Optic neuritis, Palindromic rheumatism, PANDAS (Pediatric Autoimmune Neuropsychiatric Disorders Associated with *Streptococcus*), Paraneoplastic cerebellar degeneration, Paroxysmal nocturnal hemoglobinuria (PNH), Parry Romberg syndrome, Parsonnage-Turner syndrome, Pars planitis (peripheral uveitis), Pemphigus, Peripheral neuropathy, Perivenous encephalomyelitis, POEMS syndrome, Type I, II, & III autoimmune polyglandular syndromes, Postmyocardial infarction syndrome, Postpericardiotomy syndrome, Progesterone dermatitis, Primary biliary cirrhosis, Primary sclerosing cholangitis, Psoriasis, Psoriatic arthritis, Idiopathic pulmonary fibrosis, Pyoderma gangrenosum, Pure red cell aplasia, Reactive Arthritis, Reflex sympathetic dystrophy, Relapsing polychondritis, Restless legs syndrome, Retroperitoneal fibrosis, Rheumatic fever, Schmidt syndrome, Scleritis, Sperm & testicular autoimmunity, Subacute bacterial endocarditis (SBE), Susac's syndrome, Sympathetic ophthalmia, Thrombocytopenic purpura (TTP), Tolosa-Hunt syndrome, Transverse myelitis, Type 1 diabetes, Undifferentiated connective tissue disease (UCTD) and Vesiculobullous dermatosis.

27. The method of claim 26, wherein the compound is administered intravenously.

28. A method of using a library of glucose conjugates of triptolide and analogs thereof, the method comprising screening the glucose conjugates in the library for compounds for treating cancer.

29. A method of using a library of glucose conjugates of triptolide and analogs thereof, the method comprising screening the glucose conjugates in the library for compounds for treating possible organ rejection.

30. A method of using a library of glucose conjugates of triptolide and analogs thereof, the method comprising screening the glucose conjugates in the library for compounds for treating autoimmune disease.

31. A method of synthesizing a compound according to claim 1 with $L_1$ as a direct bond, the method comprising:

reacting triptolide with 2,3,4,6-tetra-O-benzyl-D-glucopyranosyl ortho-cyclopropylethynylbenzoate to get a glucose conjugated triptolide with benzyl protecting groups; and obtaining a glucose conjugate of triptolide by removing the benzyl protecting groups.

32. A method of synthesizing a compound according to claim 1 with $L_1$ as —COCH$_2$CH$_2$CO—, the method comprising:

reacting triptolide with succinic anhydride to get a modified triptolide intermediate;

reacting the modified triptolide intermediate with a benzyl protected glucose to get a glucose conjugated triptolide with benzyl protecting groups; and obtaining a glucose conjugate of triptolide by removing the benzyl protecting groups.

33. A method of synthesizing a compound according to claim 1 with $L_1$ as —CH$_2$—, the method comprising:

reacting 2,3,4,6-tetra-O-benzyl-D-glucopyranosyl trichloroacetimidate with phenylthiomethanol to get 2,3,4,6-tetra-O-benzyl-D-glucopyranosyl phenylthiomethyl intermediate;

reacting triptolide with the 2,3,4,6-tetra-O-benzyl-D-glucopyranosyl phenylthiomethyl intermediate to get a glucose conjugated triptolide with benzyl protecting groups; and obtaining a glucose conjugate of triptolide by removing the benzyl protecting groups.

* * * * *